Figure 1:
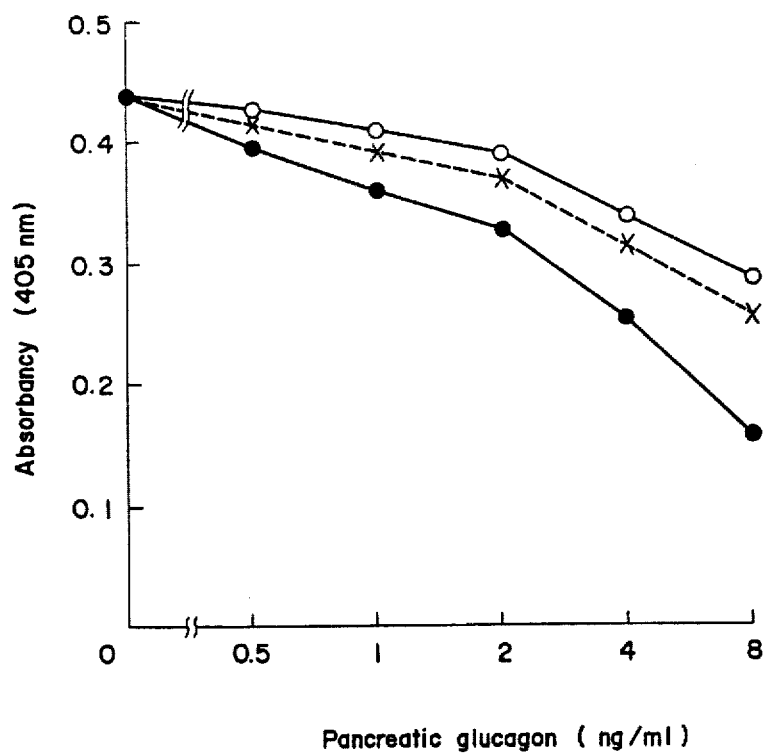

United States Patent [19]

Iwasa et al.

[11] 4,312,943
[45] Jan. 26, 1982

[54] METHOD FOR ENZYME IMMUNOASSAY OF PANCREATIC GLUCAGON

[75] Inventors: Susumu Iwasa, Kyoto; Hayao Ueno, Osaka; Mitsuhiro Wakimasu, Takarazuka, all of Japan

[73] Assignee: Takeda Chemical Industries, Ltd., Osaka, Japan

[21] Appl. No.: 69,180

[22] Filed: Aug. 24, 1979

[30] Foreign Application Priority Data

Aug. 30, 1978 [JP] Japan ................... 53/106828

[51] Int. Cl.³ ................ G01N 33/54; C12N 9/96
[52] U.S. Cl. ........................ 435/7; 435/188;
23/230 B; 424/8; 424/12; 260/112.5 R
[58] Field of Search .......... 435/7, 177, 188, 810;
424/1, 1.5, 12, 8; 23/230 B; 260/112.5

[56] References Cited

U.S. PATENT DOCUMENTS

| | | | |
|---|---|---|---|
| 3,975,342 | 8/1976 | Gross | 260/121 |
| 4,075,194 | 2/1978 | Sela et al. | 260/112.5 |
| 4,218,539 | 8/1980 | Weltman | 424/12 |
| 4,220,722 | 9/1980 | Rowley et al. | 435/7 |
| 4,221,777 | 9/1980 | Nishino | 260/121 |

OTHER PUBLICATIONS

Iwasa et al., "Enzyme Immunoassay of Pancreatic Glucagon at the Picogram Level Using B-D-Galactosudase as a Label", *Chem. Abstracts*, vol. 91, No. 25, (1979), p. 292, Abs. No. 206823h.
Schenck, "Production and Characterization of an Antiserum Against Pancreatic Glucagon", *Clin. Chim. Acta.*, vol. 80, No. 3, (1977), pp. 455–463.
Ogawa et al., "Studies on Peptides LXXVII, Synthesis of the Protected Heptadecapeptide Corresponding to Positions 13-29 of Avian Glucagon (Duck)," *Chem. Abstracts*, vol. 89, No. 21, (1978), p. 644, Abs. No. 180345k.
Imagawa et al., "Production of Anti-Glucagon Serums with a C-terminal Fragment of Pancreatic Glucagon", *Chem. Abstracts*, vol. 90, No. 23, (1979), p. 472, Abs. No. 184634x.
Ogawa et al., "Studies on Peptides LXXVII, Synthesis of the Protected Heptadecapeptide Corresponding to Positions 13-29 of Avian Glucagon (Duck)", *Chem. Pharm. Bull.*, vol. 26, No. 5, (1978), pp. 1540–1548.
Wakimasu et al., "Synthesis of the Nonacosapeptide Corresponding to the Proposed Amino Acid Sequence of Turkey Glucagon", *Chem. Absts.*, vol. 89, No. 21, (1978), p. 644, Abst. No. 180344j.
Iwasa et al., "Enzyme Immunoassay of Pancreatic Glucagon at the Picogram Level Using B-D-Galactosudase as a Label", *J. Biochem.*, vol. 86, (1979), pp. 943–949.
Imagawa et al., "Production of Anti-Glucagon Sera with a C-Terminal Fragment of Pancreatic Glucagon", *Endocrinol Japan*, vol. 26, (1979), pp. 123–131.

*Primary Examiner*—Thomas G. Wiseman
*Attorney, Agent, or Firm*—Wegner & Bretschneider

[57] ABSTRACT

A novel peptide-enzyme conjugate obtained by coupling a labeling enzyme with a peptide of the general formula:

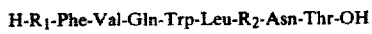

(wherein $R_1$ is a peptide fragment consisting of 1 to 10 amino acid residues in the sequence of and including the Asp in 10-position of

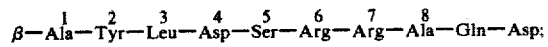

and $R_2$ is Met or Nle) is useful for a method for enzyme immunoassay of pancreatic glucagon.

20 Claims, 6 Drawing Figures

Pancreatic glucagon (ng/ml)

Wave length (nm)

METHOD FOR ENZYME IMMUNOASSAY OF PANCREATIC GLUCAGON

This invention relates to a method for enzyme immunoassay of pancreatic glucagon

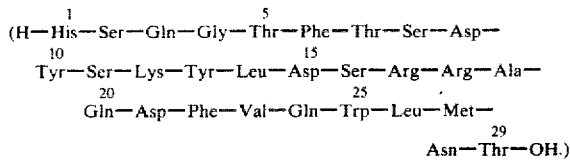

and to a peptide-enzyme conjugate usable for the method.

Pancreatic glucagon (hereinafter referred to sometimes as PG) is a hormone playing an important role in the control of blood sugar level in animals, and for an elucidation of sugar metabolic disturbance, it is essential to have an insight into the dynamics of PG secretion. It is accordingly desirable to provide an expedient, highly sensitive and specific procedure for the quantitative assay of this hormone, and radioimmunoassay procedures (hereinafter referred to briefly as RIA) are widely used today for this purpose.

However, as is well known, RIA involves the use of a radioisotope as an essential assay tool and this entails the risk of affecting the human body and that of causing environmental pollutions. The radioisotope method is further disadvantageous in that the applicable laws and regulations make it mandatory to employ special equipment as well as an inspector qualified for the operation of such equipment. As a method, which overcomes such disadvantages of RIA, is expedient to practice and gives highly reliable quantitative results, the so-called enzyme immunoassay (hereinafter referred to briefly as EIA) has come to be utilized.

The principles underlying EIA are similar to those of RIA but since an enzyme is used as a tagging or labeling agent, EIA can be expediently performed in the ordinary research laboratory or clinical laboratory. However, because the concentration of pancreatic glucagon in the blood is very low, the conventional EIA procedures, being inferior to RIA in sensitivity, have not provided satisfactory data in clinical cases.

Against the above technical background we synthesized a variety of peptides and conducted a research using them as labeled with enzymes to develop an EIA procedure which would permit a specific quantitative determination of pancreatic glucagon in a body fluid with sensitivity and accuracy which would be at least comparable to those of RIA. The research led us to the finding that a conjugated product of a labeling enzyme with a peptide which is not the same as the peptide used in the preparation of PG specific antibody is of great value for the purpose. This finding was followed by a further investigation which has culminated in the development of this invention.

Thus, the object of this invention is to provide a peptide-enzyme conjugate which is obtained by coupling a labeling enzyme with a peptide of the general formula :

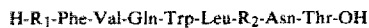

[wherein $R_1$ is a peptide fragment consisting of 1 to 10 amino acid residues in the sequence of and including Asp in 10-position of a peptide of the formula β-Ala-Tyr-Leu-Asp-Ser-Arg-Arg-Ala-Gln-Asp; and $R_2$ is Met or Nle]; and another object is to provide a method of enzyme immunoassay of pancreatic glucagon which comprises reacting a peptide-enzyme conjugate obtained by coupling a labeling enzyme with a peptide of the formula:

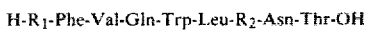

[wherein $R_1$ is a peptide fragment consisting of 1 to 10 amino acid residues in the sequence of and including the Asp in 10-position of a peptide of the formula

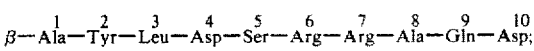

and $R_2$ is Met or Nle], a test fluid, a plasma and an anti-glucagon antibody competitively and measuring the amount of pancreatic glucagon in the test fluid by detecting the enzyme activity in the reaction system. And, further object is to provide peptides usable for the method and the conjugate. Objects of this invention other than the foregoings will be made apparent in the descriptions and claims hereinafter.

In the above-mentioned formulae, as examples of $R_1$ which denotes a peptide fragment consisting of 1 to 10 amino acid residues in the sequence of and including Asp in 10-position of the peptide β-Ala-Tyr-Leu-Asp-Ser-Arg-Arg-Ala-Gln-Asp, there may be mentioned Asp, Gln-Asp, Ala-Gln-Asp, Arg-Ala-Gln-Asp, Arg-Arg-Ala-Gln-Asp, Ser-Arg-Arg-Ala-Gln-Asp, Asp-Ser-Arg-Arg-Ala-Gln-Asp, Leu-Asp-Ser-Arg-Arg-Ala-Gln-Asp, Tyr-Leu-Asp-Ser-Arg-Arg-Ala-Gln-Asp and β-Ala-Tyr-Leu-Asp-Ser-Arg-Ala-Gln-Asp.

As one of the preferable peptide-enzyme conjugates, there may be mentioned a conjugate obtained by coupling a labeling enzyme with a peptide of the formula:

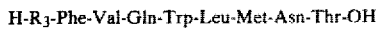

[wherein $R_3$ is a peptide fragment consisting of 1 to 7 amino acid residues in the sequence of and including the Asp in 7-position of

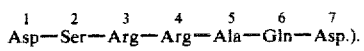

As the peptide employable in the present invention, a peptide of the formula:

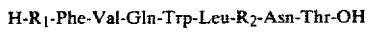

[wherein $R_1$ and $R_2$ have the same meaning as defined above] may be mentioned. And the preferable peptides employable for the purpose of the present invention, those of the following formulae may be mentioned:

H-$R_4$-Phe-Val-Gln-Trp-Leu-Met-Asn-Thr-OH wherein $R_4$ is Asp or β-Ala-Tyr-Leu-Asp-Ser-Arg-Arg-Ala-Gln-Asp and H-$R_5$-Phe-Val-Gln-Trp-Leu-Nle-Asn-Thr-OH wherein $R_5$ is Asp, Asp-Ser-Arg-Arg-Ala-Gln-Asp, or β-Ala-Tyr-Leu-Asp-Ser-Arg-Arg-Ala-Gln-Asp.

Throughout this specification and claims, when amino acids, peptides, protective groups, reactive groups, etc. are represented by abbreviations, these abbreviations are either those according to IUPAC-IUB Commission on Biological Nomenclature or those in routine use in this field of art, Some such abbreviations are given below. It should also be noted that where optical isomerism is involved as to amino acids, etc., the L-forms are usually meant unless otherwise indicated.

Arg: Arginine
Trp: Tryptophan
Asn: Asparagine
Asp: Aspartic acid
Thr: Threonine
Ser: Serin
Glu: Glutamic acid
Gln: Glutamine
Ala: Alanine
Val: Valine
Met: Methionine
Met(O): Methionine sulfoxide
Leu: Leucine
Tyr: Tyrosine
β-Ala: β-Alanine
Nle: Norleucine
Phe: Phenylalanine
Z: Carbobenzoxy
Boc: t-Butyloxycarbonyl
OBu$^t$: t-Butyl ester
OBzl: Benzyl ester
ONB: N-hydroxy-5-norbornene-2,3-dicarboximide ester
MBS: p-Methoxybenzenesulfonyl
HONB: N-hydroxy-5-norborene-2,3-dicarboximide
DCC: N,N'-dicyclohexylcarbodiimide
DCU: N,N'-dicyclohexylurea
DMF: N,N-dimethylformamide
NMP: N-methyl-2-pyrrolidone
TFA: Trifluroacetic acid
THF: Tetrahydrofuran
TEA: Triethylamine
DCHA: dicyclohexylamine
CMC: Carboxymethyl-cellulose
ECDI: 1-Ethyl-3-(3-dimethylaminopropyl)-carbodiimide
CMCT: 1-Cyclohexyl-3-(2-morpholinoethyl)-carbodiimidometho-p-toluenesulfonate
GLA: Glutaraldehyde
m-MBHS: meta-Maleimidobenzoyl-N-hydroxysuccinimide ester
p-MCHS: para-Meleimidomethylcyclohexane-1-carboxyl-N-hydroxysuccinimide ester
EDTA: Ethylenediamine tetraacetate disodium 2H$_2$O
HSA: Human serum albumin
BSA: Bovine serum albumin The various peptides which are useful for the purposes of this invention can be prepared by procedures known per se in the art of peptide synthesis. Thus, both the solid phase and liquid phase method may be employed, although the liquid phase method proves advantageous in many instances. Such method for peptide synthesis are found in the literature such as Schröder and Lubke: The Peptides, Vol. 1(1966), Academic Press, New York, U.S.A.; Izumiya et al.: "Peptide Gose" (Pentide Synthesis), Maruzen Inc., Japan (1975). M. Bodansky and M. A. Ondetti: Peptide Synthesis, Interscience, New York, 1966; or F. M. Finn and K. Hofman: The Proteins, vol. 2, ed. by H. Nenrath, R. L. Hill, Academic Press Inc., New York, 1976. Thus, there may be mentioned the azide method, chloride method, acid anhydride method, mixed acid anhydride method, DCC method, active ester method, the method involving the use of Woodward's Reagent K, carbodiimidazole method, reduction-oxidation method, DCC/additive (e.g. HONB, HOBt, HOSu) method etc.

The peptide usable for the present invention can be produced by condensing a starting material having a reactive carboxyl group, which corresponds to either one of the two fragments of the peptide as divided at an optional one of the peptide-linkages, with a mating starting material having a reactive amino group, which corresponds to the other of said two fragments, in a manner conventional per se and, if the resulting condensation product carries a protective group or protective groups, removing such protective group or groups in a manner conventional per se.

In carrying out the reaction for the production of the peptide, it is normally preferable that Asp be previously protected. In many cases, the contemplated product is obtained on removal, in the final step, of protective groups from the peptide as protected in at least one of the constituent amino acid residues of the peptide. The protection of functional groups which should not be involved in the reaction and which may be present in starting materials, the protective groups useful for the purpose, the removal of such protective groups, the activation of functional groups to be involved in the reaction, etc. may be carried out in manners conventional per se or be selected from among the known groups.

As examples of the amino-protecting groups useful for the protection of amino groups in the starting materials, there may be mentioned carbobenzoxy, t-butyloxycarbonyl, t-amyloxycarbonyl, isobornyloxycarbonyl, p-methoxybenzyloxycarbonyl, 2-chlorobenzyloxycarbonyl, admantyloxycarbonyl, trifluoroacetyl, phthalyl, formyl, o-nitrophenylsulfenyl, diphenylphosphinothioyl, etc. As examples of carboxyl-protecting groups, there may be mentioned such ester-forming groups as those capable of giving alkyl esters (e.g. methyl, ethyl, propyl, butyl, t-butyl, etc. esters), benzyl ester, p-nitrobenzyl ester, p-methoxybenzyl ester, p-chlorobenzyl ester, benzhydryl ester, etc. and hydrazide-forming groups such as those capable of giving carbobenzoxy hydrazide, t-butyloxy-carbonyl hydrazide, trityl hydrazide, etc. As groups for protecting the guanidino group of Arg, there may be mentioned nitro, tosyl, p-methoxybenzenesulfonyl, carbobenzoxy, isobornyloxycarbonyl, admantyloxycarbonyl, etc. The guanidino group may also be protected in the form of a salt with an acid (e.g. benzenesulfonic acid, toluenesulfonic acid, hydrochloric acid, sulfuric acid, etc.).

The hydroxyl groups of Thr may be protected, for example by way of known esterification or etherification. As examples of groups suitable for said esterification, there may be mentioned lower alkanoyl groups (e.g. acetyl), aroyl groups (e.g. benzoyl), and groups derived from carbonic acid, such as benzyloxycarbonyl, ethyloxycarbonyl, etc. As groups suitable for said etherification, there may be mentioned benzyl, tetrahydropyranyl, t-butyl, etc. The hydroxyl group of Thr, however, need not necessarily be protected. Met may be previously protected in the form of a sulfoxide. As examples of the activated carboxyl group in the starting material, there may be mentioned the corresponding acid anhydride, azide, active ester (e.g. esters with pentachlorophenol, p-nitrophenol, N-hydroxysuccinimide, N-hydroxybenzotriazole, N-hydroxy-5-norbornene-2,3-dicarboximide, etc.).

Some reactions for the formation of peptide bonds may be conducted in the presence of a dehydrating agent (such as carbodiimide reagents, e.g. dicyclohexylcarbodiimide; carbodiimidazole, etc.). The condensation reaction for the production of the peptide can be carried out in the presence of a solvent. The solvent may be selected from among the solvents which are known to be useful for the purpose of peptide-forming condensation reactions. Thus, for example, dry or aqueous dimethylformamide, dimethylsulfoxide, pyridine, chloroform, dioxane, dichloromethane, tetrahydrofuran, ethyl acetate, N-methylpyrrolidone, etc. as well as suitable mixtures thereof may be mentioned.

The reaction temperature may be selected from the range known to be useful for the purpose of peptide-forming condensation reactions. Thus, it may normally be within the range of about $-40°$ C. to about 60° C. and, preferably about $-20°$ C. to about 0° C.

After the condensation reaction, any protective group or groups that may exist on the product peptide can be removed by conventional procedures. As examples of such known procedures, there may be mentioned reductive procedures (e.g. hydrogenation with a catalyst such as palladium black, reduction with sodium metal in liquid ammonia), acidolysis (e.g. acidolysis with a strong acid such as trifluoroacetic acid, hydrogen fluoride, methanesulfonic acid, etc.) and so forth.

The peptide produced in the above manner can be isolated from the reaction mixture by known peptide-separation procedures (e.g. extraction, distribution, column chromatography, etc.).

Since the peptide contains arginine residues, it may be isolated in the form of a salt. As examples of acids capable of forming such salts, there may be mentioned inorganic acids such as hydrochloric acid, hydrobromic acid, nitric acid, sulfuric acid, phosphoric acid, etc. and organic acids such as formic acid, acetic acid, propionic acid, lactic acid, citric acid, oxalic acid, maleic acid, etc.

The starting materials for the production of the peptide of this invention can also be prepared by the above-mentioned conventional procedures for peptide synthesis, i.e. by condensing amino acids in accordance with the amino acid sequence of each starting material.

The present method for EIA of pancreatic glucagon is applicable to (1) the assay of pancreatic glucagon in a test fluid such as plasma which comprises adding a known amount of a peptide-enzyme conjugate and a known amount of an insoluble PG-specific antibody to a fluid containing an unknown amount of pancreatic glucagon, and determining the enzyme activity of the peptide-enzyme conjugate in the liquid phase or of the reacted peptide-enzyme conjugate on the solid phase [FEBS Letters 15, 232(1971)]; (2) the assay of pancreatic glucagon in a test fluid which comprises adding a known amount of a peptide-enzyme conjugate and a known amount of a soluble PG-specific antibody to a test fluid containing pancreatic glucagon to cause a competitive binding reaction to take place, then adding a known amount of a second antibody insoluble in the first antibody [i.e. when, for instance, said PG-specific antibody has been prepared using a rabbit, an anti-rabbit immunoglobulin G (IgG) antibody] and, in the same manner as in (1) determining the enzyme activity in the liquid phase or on the solid phase [FEBS Letters, ibid.], and (3) the assay of pancreatic glucagon in a test fluid which comprises adding a known amount of a peptide-enzyme conjugate and a known amount of a soluble PG-specific antibody to a test fluid containing pancreatic glucagon so as to cause a competitive binding reaction to take place in the same manner as in (2) adding a known amount of a second antibody and, when the second antibody is an anti-animal (e.g. rabbit) IgG antibody, a normal animal (e.g. rabbit) serum to cause a precipitation reaction to take place and determining the enzyme activity in the liquid phase or on the solid phase as described above in (1) [Clinica Chimica Acta 67, 263 (1976). ]. In any of the above processes, it is advantageous to carry out an activity determination on the solid phase, for when the enzyme activity of the liquid phase is measured, the impurities in the test fluid may interfere with results. From reproducibility and sensitivity points of view, the "double antibody procedures" which permit a determination with a small amount of a PG-specific antibody, namely the above methods (2) and (3), are more desirable.

In any of the above method, only if the affinity of the peptide-enzyme conjugate for the antibody can be reduced with respect to that of pancreatic glucagon, the coupling of the conjugate with the antibody in these assay systems is readily replaced by a small amount of pancreatic glucagon, with the result that even very low concentrations of pancreatic glucagon can be detected and assayed.

The enzyme used as the labeling agent should only be a stable one having a high specific activity. Thus, for example, peroxidase, $\beta$-D-galactosidase, $\beta$-D-glucosidase, $\beta$-glucuronidase, alkaline phosphatase, glucoamylase, $\alpha$-amylase, Taka-amylase A, urease, cholinesterase, etc may prove useful, although $\beta$-D-galcatosidase or alkaline phosphatase may be desirably employed among others.

In preparing the peptide-enzyme conjugate according to this invention, the substituent groups present in the peptide and enzyme, such as amino, carboxyl, hydroxy or/and sulfhydryl groups, cna be utilized. As examples of the condensing reagent, there may be mentioned (i) water-soluble carbodiimide reagents, e.g. ECDI and CMCT, which are capable of combining the reactive amino group in the peptide or enzyme with the reactive carboxyl group in the counterpart in an aqueous solvent with the elimination of water, (ii) the N-hydroxysuccimimide ester-maleimidating reagents, e.g. m-MBHS and p-MCHS, which are capable of maleimidating the reactive amino group of the peptide through a reaction of the latter with an activated ester of N-hydroxysuccinimide and allowing the maleimidated amino group to attach itself to the sulfhydryl group of the enzyme, and (iii) the dialdehyde reagents, e.g. succindialdehyde and GLA, which are capable of causing the reactive amino group of the peptide or enzyme to combine with the reactive amino group of the counterpart material.

The coupling or condensation reaction between the peptide and enzyme may be carried out with any condensing agent which is useful for condensation of the two materials, although the aforementioned carbodiimide, maleimide and dialdehyde reagents are preferred. The condensation reaction may be conducted in an aqueous solvent, which may be selected from among the solvents known to be useful for condensation between a peptide and an enzyme. As examples of such solvent may be mentioned phosphate buffer in the pH range of pH 6 to pH 8 and borate buffer in the range of pH 7 to pH 9.

The duration of said condensation reaction between the peptide and enzyme is normally somewhere between 30 minutes to 20 hours. In consideration of the stability of the enzyme, the reaction time is preferably 30 minutes to 3 hours. However, at a low temperature, the reaction may be carried out over a fairly protracted time of 2 to 4 days. Normally, the reaction temperature may range from about 4° C. to 50° C. and, preferably, from about 15° C. to 30° C.

Following the condensation reaction, the product peptide-enzyme conjugate can be purified and recovered by column chromatography on a proper molecular sieve, e.g. Sephadex G100 or G200 (Pharmacia Fine Chemicals), Sepharose 6B or 4B (Pharmacia Fine Chemicals) or the like.

As examples of the peptide-enzyme conjugate suitable for the purposes of this invention, the following conjugate may be mentioned. For an assay of pancreatic glucagon with the 30K, G21, G7, R517 or other antibody prepared by immunizing rabbits with pancreatic glucagon, a highly sensitive result can be obtained with the peptide-enzyme conjugate prepared by condensing an enzyme with a peptide of the formula

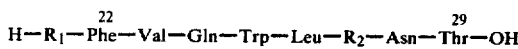

(wherein $R_1$ is a peptide fragment consisting of 1 to 9 amino acid residues up to the 21-position of pancreatic glucagon; and $R_2$ is Met or Nle). Particularly desirable is the conjugate of an enzyme with a peptide of the formula

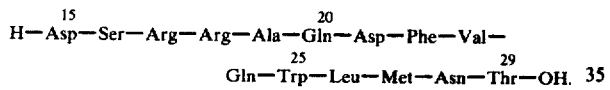

For an assay of pancreatic glucagon with the N6C, N6E or N16a antibody obtained by immunizing rabbits with a peptide of the formula

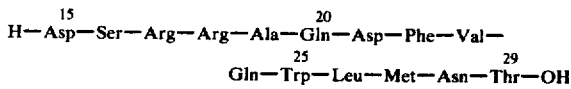

or a peptide of the formula

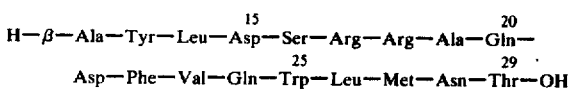

a highly sensitive result can be obtained with the peptide-enzyme conjugate prepared by condensing an enzyme with a peptide of the formula

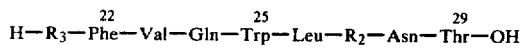

(where $R_3$ is a peptide fragment consisting of 1 to 7 amino acid residues up to the 21-position of pancreatic glucagon; and $R_2$ is Met or Nle). A particularly sensitive result can be obtained with the conjugate of an enzyme with a peptide of the formula H—Asp—Phe—Val—Gln—Trp—Leu—Met—Asn—Thr—OH
  21              25                    29
or a peptide of the formula H—Asp—Ser—Arg—Arg—Ala—
                                                    15

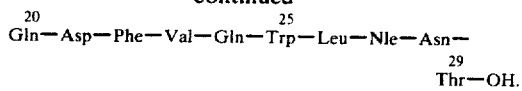

The antibody to be employed according to this invention may be any of the antibodies reactive to pancreatic glucagon and to the peptide-enzyme conjugate. Thus, for example, 30K of Unger et al. (Diabetes, Vol. 17 (1968), P. 321), G21 of Ohneda et al (Diabetes, Vol. 18(1969), P. 1), G7 of Ohneda et al (Hormone and Metabolic Research, Vol. 8 (1976) p. 170), R517 of Sakurai et al. ["Naika Hokan", Vol. 23 (1975), P. 247 or Japanese Journal of Nuclear Medicine 10, p. 135 (1973)] and the N6C, N6E and N16a PG-specific antibody which are used in Reference Example 4 and Example 13 hereinafter can be successfully employed.

The second antibody used according to this invention can be prepared by a multiple injection of the IgG of a certain species of animal (e.g. rabbit) which has been used in the preparation of the anti-PG antibody into a different species of animal (e.g. goat). The immunizing procedure may be any of the known antibody preparation procedures. Thus, for example, a satisfactory antibody can be obtained by 4 subcutaneous administrations of about 2 mg each of IgG together with Freund's complete adjuvant at intervals of 3 weeks. The commercial anti-rabbit IgG serum (goat) (Miles Laboratories, Inc. U.S.A.) may also be employed.

The insoluble second antibody can be obtained by salting out the above-obtained anti-IgG serum with sodium sulfate or ammonium sulfate, carrying out a column chromatography on ion exchanger such as DEAE-cellulose to obtain the IgG-fraction of anti-IgG serum and coupling the same with a solid phase such a BrCN-activated polysaccharide such as cellulose or Sephadex (FEBS Letters 15 (1971), p. 232). Alternatively the above-mentioned IgG fraction of antiserum may be contacted with glass rods, silicone-rubber strings or polystyrene balls to physically adsorb the second antibody thereon ("Kagaku-to-Seibutsu" (Chemistry and Biology) 14 (1976), p. 741).

The plasma to be used in the EIA method according to this invention may be any plasma that is useful as a test plasma. Thus, the plasma specimens of mammalian animals including man, rat, mouse and guinea pig may be mentioned. Usually, however, human plasma is employed in order to study the behavior of pancreatic glucagon in human plasma.

The assay method of this invention is of great practical value, for it yields highly sensitive and specific results as compared with the conventional EIA of pancreatic glucagon. The sensitivity is, in fact, comparable to that of RIA, and this fact means that the EIA according to this invention can be conveniently employed, even in clinical laboratories not equipped for radioisotope (hereinafter referred to as RI) control in lieu of RIA which involves various drawbacks associated with the use of a RI for an expedient quantitative assay of pancreatic glucagon in the blood. Unlike RI which has a half-life, the peptide-enzyme complex of this invention is so stable that it permits measurements on a large number of test specimens with the same lot, thus giving results with excellent reproducibility.

The following examples and reference examples are intended to describe this invention in further detail without limiting its scope as recited in the claims.

In the following Examples, thinlayer chromatographic data are obtained by using Silica-gel Plate 60 F$_{254}$, Merck or Cellulose Plate Avicel SF, Funakoshi Yakuhin K.K., Japan and the following developer solvent systems.

Rf$^1$ = chloroform-methanol-acetic acid = 9:1:0.5
Rf$^2$ = chloroform-methanol-water = 7:3:0.5
Rf$^3$ = n-butanol-pyridine-acetic acid-water = 30:20:6:24

EXAMPLE 1

Production of

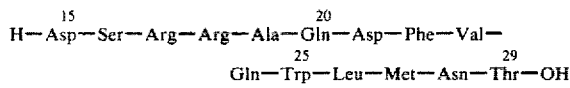

[hereinafter referred to as "peptide(I) (15-29)"] (1) Preparation of Boc-Asn-Thr-OBzl In 300 ml of TFA is dissolved 112 g of Boc-Thr-OBzl and the solution is stirred at room temperature for 20 minutes. Following addition of 30 ml of concentrated hydrochloric acid, the solution is concentrated under reduced pressure. The residue is dissolved in 1 l of THF, and under ice-cooling, the solution is neutralized with 50 ml of TEA. To this solution are added 76.7 g of Boc-Asn-OH, 64.5 g of HONB and 74.3 g of DCC, followed by stirring for 15 hours. The precipitated DCU is filtered off, the solvent distilled off under reduced pressure and the residue dissolved in 1 l of ethyl acetate. The solution is washed with 10 % aqueous citric acid (300 ml×3), saturated aqueous sodium hydrogen carbonate (300 ml×3) and water (300 ml×3) in the order mentioned, and dried over anhydrous sodium sulfate. The solvent is distilled off under reduced pressure and the residue is treated with 1 l of diethyl ether. The resultant powders are collected by filtration and recrystallized from acetonitrile. Yield 105.1 g (75.2%); m.p. 165°–166° C.; $[\alpha]_D^{23}$ −13.9°(c=0.9, DMF); Rf$^1$ = 0.51.

Elemental analysis—Calcd. (for C$_{20}$H$_{29}$O$_7$N$_3$): C, 56.75; H, 6.90; N, 9.92; Found: C, 57.01; H, 6.89; N, 9.94.

(2) Preparation of Boc-Met(O)-Asn-Thr-OBzl

To 50.0 g of Boc-Asn-Thr-OBzl is added 170 ml of TFA and the mixture is shaken at room temperature for 30 minutes. The solution is concentrated and treated with 500 ml of diethyl ether. The resultant powder is collected by filtration and dried. It is dissolved in 400 ml of THF, and under ice-cooling 20 ml of TEA is added. To this solution is added Boc-Met(O)-ONB (prepared by dissolving 31.3 g of Boc-Met(O).OH and 23.3 g of HONB in 200 ml of THF, adding 26.8 g of DCC under ice-cooling and stirring the mixture for 4 hours). The mixture is stirred for 15 hours, after which time the solvent is distilled off under reduced pressure. To the residue are added ethyl acetate (200 ml) and ether (200 ml), and the resultant powders are collected by filtration and reprecipitated from acetonitrile. Yield 48.5 g (72.0%), m.p. 145°–147° C., $[\alpha]_D^{23}$ −6.5° (c=1.1, DMF), Rf$^1$ = 0.19.

Elemental analysis—Calcd. (for C$_{25}$H$_{38}$O$_9$N$_4$S): C, 52.62; H, 6.71; N, 9.82; S, 5.62; Found: C, 52.44; H, 6.73; N, 9.60; S, 5.15.

(3) Preparation of Boc-Leu-Met(O)-Asn-Thr-OBzl

To 15.0 g of Boc-Met(O)-Asn-Thr-OBzl is added 45 ml of TFA and the mixture is shaken at room temperature for 45 minutes. The mixture is then concentrated and precipitated with 100 ml of ether. The resultant powders are collected by filtration, dried and dissolved in 50 ml of DMF. The solution is cooled with ice, and following addition of 5.7 ml of TEA, there is added Boc-Leu-ONB (prepared from 6.69 g of Boc-Leu-OH, 5.70 g of HONB and 6.56 g of DCC). The mixture is stirred for 15 hours, at the end of which time the solvent is distilled off under reduced pressure. To the residue is added 200 ml of ethyl acetate and the resultant powders are collected by filtration and reprecipitated from acetonitrile-ethyl acetate. Yield 15.0 g (83.4%); m.p. 134°–136° C.; $[\alpha]_D^{24}$ −15.1° (c=1.0, DMF); Rf$^1$ = 0.25.

Elemental analysis—Calcd. (for C$_{31}$H$_{49}$O$_{10}$N$_5$S): C, 54.45; H, 7.22; N, 10.24; S, 4.69; Found: C, 54.62; H, 7.60; N, 9.89; S, 3.95.

(4) Preparation of Z-Gln-Trp-OBzl

In 500 ml of THF is dissolved 50.0 g of H-Trp-OBzl·p-toluenesulfonate, and under ice-cooling, 15.4 ml of TEA, 28.0 g of Z-Gln-OH, 19.7 g of HONB and 22.7 g of DCC are added. The mixture is stirred for 15 hours. The precipitated DCU is filtered off, the filtrate concentrated and the residue dissolved in 300 ml of ethyl acetate. The solution is washed with saturated aqueous sodium hydrogen carbonate (150 ml×2), 10% aqueous citric acid (150 ml×2) and water (150 ml×2) in the order mentioned. The solvent is distilled off under reduced pressure, the residue dissolved in 300 ml of THF and the insolubles are filtered off. The filtrate is concentrated and precipitated with 500 ml of diethyl ether. The resultant powders are collected by filtration and recrystallized from acetonitrile. Yield 46.1 g (82.8%); $[\alpha]_D^{23}$ +5.8°(c=1.0, DMF); Rf$^1$ = 0.60.

Elemental analysis—Calcd. (for C$_{31}$H$_{32}$O$_6$N$_4$): C, 66.89; H, 5.80; N, 10.07; Found: C, 66.79; H, 5.71; N, 10.20.

(5) Preparation of Z-Val-Gln-Trp-OH

In 700 ml of methanol is dissolved 50.0 g of Z-Gln-Trp-OBzl, and catalytic reduction (catalyst: palladium black) is carried out for 5 hours. The crystalline precipitate is collected by filtration and suspended in 300 ml of DMF. The suspension is dissolved by the addition of 13 ml of TEA and the catalyst is filtered off. To the filtrate is added 37.0 g of Z-Val-ONB, and after 10 hours' stirring, the mixture is neutralized with 100 ml of 1N-hydrochloric acid, followed by addition of 500 ml of water. The resultant powders are collected by filtration and washed well with methanol. Yield 43.0 g (84.7%); m.p. 246°–247° C; $[\alpha]_D^{23}$ +12.4°(c=0.9, DMF); Rf$^1$ = 0.14.

Elemental analysis—Calcd. (for C$_{29}$H$_{35}$O$_7$N$_5$): c, 61.58; H, 6.24; N, 12.38; Found: C, 61.86; H, 6.30; N, 12.36.

(6) Preparation of Z-Phe-Val-Gln-Trp-OH

In 100 ml of acetic acid is dissolved 5.1 g of Z-Val-Gln-Trp-OH and catalytic reduction is carried out for 3 hours. The catalyst is filtered off and the filtrate is concentrated and suspended in 200 ml of DMF. To this suspension is added 2 ml of TEA, and Z-Phe-ONB which has been prepared from 2.70 g of Z-Phe-OH, is further added. The mixture is stirred for 7 hours. The solvent is then distilled off under reduced pressure, aqueous acetic acid is added to the residue, and the resultant gel is collected by filtration and reprecipitated from methanol. Yield 5.50 g (84.5%); m.p. 240° C.; $[\alpha]_D^{24}$ +4.1°(c=1.0, DMF); Rf$^1$ = 0.15.

Elemental analysis—Calcd. (for C$_{38}$H$_{44}$O$_8$N$_6$·½H$_2$O): C, 63.23; H, 6.28; N, 11.64; Found: C, 63.11; H, 6.29; N, 11.80.

(7) Preparation of Boc-Asp(OBzl)-Phe-Val-Gln-Trp-OH

In a mixture of 150 ml of DMF and 50 ml acetic acid is dissolved 8.5 g of Z-Phe-Val Gln-Trp-OH and catalytic reduction is carried out for 5 hours. The catalyst is filtered off, the filtrate is concentrated and the residue is precipitated with 100 ml of methanol. The crystals thus obtained are suspended in 200 ml of DMF, followed by addition of 3.0 ml of TEA and Boc-Asp(OBzl)ONB (prepared from 3.9 g of Boc-Asp(OBzl)-OH, 2.4 g of HONB and 2.7 g of DCC). The mixture is stirred for 10 hours, at the end of which time the solvent is distilled off under reduced pressure. To the residue is added aqueous acetic acid and the resultant gel is collected by filtration and reprecipitated from DMf-water. Yield 6.3 g (58.1%); m.p. 191°–192° C. (decomp.); $[\alpha]_D^{24} - 6.2°(c=1.1, DMF)$; $Rf^1 = 0.11$.

Elemental analysis—Calcd. (for $C_{46}H_{57}O_{11}N_7.3/2-H_2O$): C, 60.64; H, 6.63; N, 10.76; Found: C, 60.30; H, 6.48; N, 11.34.

(8) Preparation of Boc-Gln-Asp(OBzl)-Phe-Val-gln-Trp-OH To 6.0 g of Boc-Asp(OBzl)-Phe-Val-Gln-Trp-OH is added 50 ml of TFA in a current of nitrogen gas, and after shaking for 10 minutes, the mixture is concentrated and treated with diethyl ether. The resultant powders are collected by filtration and dissolved in 100 ml of DMF, followed by addition of 20 ml of TEA and Boc-Gln-ONB (prepared from 1.76 g of Boc-Gln-OH, 1.34 g of HONB and 1.54 g of DCC). The mixture is stirred for 15 hours at the end of which time aqueous acetic acid is added. The resultant powders are collected by filtration and reprecipitated from acetonitrile-water. Yield 5.50 g (82.6%); m.p. 210°–212° C.(decomp.); $[\alpha]_D^{24} - 10.1°(c=1.1, DMf)$; $Rf^1 = 0.09$ Elemental analysis—Calcd. (for $C_{51}H_{65}O_{13}N_9$): C, 60.52; H, 6.47; N, 12.46; Found: C, 60.19; H, 6.37; N, 12.23.

(9) Preparation of Z-Arg(MBX)-Ala-OBu$^t$

In 300 ml of methanol is dissolved 31.0 g of Z-Ala-OBu$^t$ and catalytic reduction is carried out for 5 hours. The catalyst is filtered off and the filtrate concentrated. Separately, 53.0 g of Z-Arg(MBS)-OH.DCHA is suspended in 500 ml of ethyl acetate and shaken well with 200 ml of 10% citric acid. The solution is washed with water, dried over anhydrous sodium sulfate and dissolved in 500 ml of THF. To this solution is added the H-Ala-OBu$^t$ prepared above, followed by addition of 14.9 g of HONB. Under ice-cooling, 17.1 g of DCC is added and the mixture is stirred for 10 hours. The precipitated DCU is filtered off and the filtrate is concentrated and dissolved in 500 ml of ethyl acetate. The solution is washed with 10% aqueous citric acid (200 ml×3), saturated aqueous sodium hydrogen carbonate (200 ml×3) and water (200 ml×3), and dried over anhydrous sodium sulfate. The solvent is distilled off under reduced pressure, 300 ml of diethyl ether is added to the residue and the resultant powders are recovered by filtration. Yield 44.5 g (66.8%); m.p. 126°–127° C.;$[\alpha]_D^{25} - 6.0°(c=1.0, DMF)$; $Rf^1 = 0.62$.

Elemental analysis—Calcd. (for $C_{28}H_{39}O_8N_5S$): C, 55.52; H, 6.49; N, 11.56; S, 5.27; Found: C, 55.71; H, 6.49; N, 11.81; S, 5.29.

(10) Preparation of Z-Arg(MBS)-Arg(MBS)-Ala-OBu$^t$

In 500 ml of methanol is dissolved 43 g of Z-Arg(MBS)-Ala-OBu$^t$ and catalytic reduction is carried out for 5 hours. The reaction mixture is concentrated and the residue is dissolved in 200 ml of DMF. To this solution are added Z-Arg(MBS)-OH [prepared from 49.7 g of Z-Arg(MBS)-OH.DCHA] and 14.0 g of HONB. Then, under ice-cooling, 16.1 g of DCC is added and the mixture stirred for 15 hours. The precipitated DCU is filtered off, the filtrate concentrated and the residue dissolved in 500 ml of chloroform. The solution is washed with 10% aqueous citric acid (300 ml×3), saturated aqueous sodium hydrogen carbonate (300 ml×3) and water (300 ml×3) in the order mentioned, and dried over magnesium sulfate. The solvent is distilled off under reduced pressure and 300 ml of methanol is added. The resultant crystals are recovered by filtration and recrystallized from methanol. Yield 52.4 g (79.2%); m.p. 116°–118° C.; $[\alpha]_D^{25} - 8.8°(c=1.0, DMF)$; $Rf^1 = 0.42$.

Elemental analysis—Calcd. (for $C_{41}H_{57}O_{12}LN_9S_2.2H_2O$): C, 50.86; H, 6.35; N, 13.02; S, 6.62; Found: C, 51.05; H, 6.08; N, 13.11; S, 6.62.

(11) Preparation of boc-Ser-Arg(MBS)-Arg(MBS)-Ala-OBu$^t$

In a mixture of 80 ml DMF and 300 ml methanol is dissolved 30.0 g of Z-Arg(MBS)-Arg(MBS)-Ala-OBu$^t$ and catalytic reduction is carried out for 7 hours. The catalyst is filtered off, the methanol distilled off under reduced pressure, and 7.3 g of Boc-Ser-OH and 6.3 g of HONB are added. Under ice-cooling, 7.3 g of DCC is added and the mixture stirred for 10 hours. The precipitated DCU is filtered off, the solvent distilled off under reduced pressure and the residue dissolved in 500 ml of chloroform. The solution is washed with saturated sodium hydrogen carbonate (300 ml×2) and water (300 ml×2), followed by drying over magnesium sulfate. The solvent is distilled off under reduced pressure, the residue is dissolved in 30 ml of chloroform and run onto a column of silica gel (400 g). The chromatogram is developed with a solvent system of chloroform-methanol-acetic acid (9:0.7:0.35) and the fractions between 800 ml and 2 l are pooled, concentrated and precipitated with diethyl ether to obtain powders. Yield 25.5 g (79.0%); m.p. 85°–88° C.; $[\alpha]_D^{26} - 20.9°(c=1.0, methanol)$; $Rf^1 = 0.33$.

Elemental analysis—Calcd. (for $C_{41}H_{64}O_{14}N_{10}S_2$. $H_2O$): C, 49.09; H, 6.63; N, 13.96; S, 6.39; Found: C, 48.96; H, 6.55; N, 13.70; S, 5.84.

(12) Preparation of Boc-Asp(OBzl)-Ser-Arg(MBS)-Arg(MBS)-Ala-OH

To 10.5 g of Boc-Ser-Arg(MBS)-Arg(MBS)-Ala-OBu$^t$ is added 50 ml of TFA, and the mixture is shaken at room temperature for 60 minutes and, then, concentrated. The concentrate is then treated with 300 ml of ether and the resultant powders are collected by filtration and dissolved in 50 ml of DMF. To this solution are added 4.1 ml of TEA and Boc-Asp(OBzl)-ONB (prepared from 3.40 g of Boc-Asp(OBzl).OH, 1.97 g of HONB and 2.27 g of DCC), and the mixture is stirred for 15 hours. The solvent is distilled off under reduced pressure, aqueous acetic acid is added to the residue and the resultant powders are collected by filtration, dried and reprecipitated from acetonitrile-ether. Yield 6.0 g (51.5%); m.p. 126°–130° C.; $[\alpha]_D^{24} + 3.5°(c=1.0, DMF)$; $Rf^1 = 0.17$.

Elemental analysis—Calcd. (for $C_{48}H_{67}O_{17}N_{11}S_2.2H_2O$): C, 49.26; H, 6.12; N, 13.17; S, 5.48; Found: C, 49.62; H, 5.84; N, 13.00; S, 5.03.

(13) Preparation of Boc-Gln-Asp(OBzl)-Phe-Val-Gln-Trp-Leu-Met(O)-Asn-Thr-OBzl

To 3.25 g of Boc-Leu-Met(O)-Asn-Thr-OBzl is added 25 ml of TFA and the mixture is shaken at room temperature for 15 minutes, after which it is concentrated. To the residue is added 100 ml of diethyl ether and the resultant powders are collected by filtration and dried. The powders are dissolved in 10 ml of NMP, the solution is shaken well with 2 ml of TEA, and 100 ml of diethyl ether is added. The resultant powders are recovered again by filtration and dissolved in 100 ml of DMF. In this solution are further dissolved 4.80 g of Boc-Gln-Asp-(OBzl)-Phe-Val-Gln-Trp-OH and 2.70 g of HONB. Under ice-cooling, 1.55 g. of DCC is added and the mixture is stirred for 58 hours. From the resultant gel, the solvent is distilled off under reduced pressure and the residue is thoroughly washed with aqueous acetonitrile. Yield 5.75 g (76.8%), m.p. 234° C. (decomp.), $[\alpha]_D^{26} -15.8°(c=0.4,$ acetic acid), $Rf^2 = 0.63$.

Elemental analysis—Calcd. (for $C_{77}H_{104}O_{20}N_{14}S$): C, 58.61; H, 6.64; N, 12.43; S, 2.03; Found: C, 59.13; H, 6.96; N, 12.40; S, 1.70.

(14) Preparation of Boc-Asp(OBzl)-Ser-Arg(MBS)-Arg(MBS)-Ala-Gln-Asp(OBzl)-Phe-Val-Gln-Trp-Leu-Met(O)-Asn-Thr-OBzl To 5.20 g of Boc-Gln-Asp(OBzl)-Phe-Val-Gln-Trp-Leu-Met(O-Asn-Thr-OBzl is added 1 ml of anisole and, in nitrogen gas streams 35 ml of TFA is added. The mixture is stirred at room temperature for 15 minutes, after which it is concentrated. To the residue is added 100 ml of diethyl ether and the resultant powders are collected by filtration and dissolved in 20 ml of NMP. To this solution is added 2.77 ml of TEA and after thorough shaking, 200 ml of diethyl ether is added. The resultant powders are recovered by filtration and dissolved in 150 ml of DMF. To this solution are added 3.66 g of Boc-Asp(OBzl)-Ser-Arg(MBS)-Arg(MBS)-Ala-OH and 2.36 g of HONB and under cooling with ice-NaCl at −10° C., 1.02 g of DCC is added. The reaction mixture is stirred at 0° C. for 10 hours and at room temperature for 24 hours. The precipitated DCU is filtered off and the solvent is distilled off under reduced pressure. To the residue is added 50 ml of water and the resultant powders are recovered by filtration and washed well with aqueous acetonitrile. Yield 5.3 g (61.1%); m.p. 237° C.(decomp.); $[\alpha]_D^{26} -7.1°(c=0.9,$ acetic acid); $Rf^2 = 0.63$ Elemental analysis—Calcd. (for $C_{120}H_{161}O_{34}N_{25}S_3 \cdot 2H_2O$): C, 54.82; H, 6.32; N, 13.32; S, 3.57; Found: C, 54.47; H, 6.16; N, 13.07; S, 3.47.

(15) Preparation of H-Asp-Ser-Arg-Arg-Ala-Gln-Asp-Phe-Val-Gln-Trp-Leu-Met(O)-Asn-Thr-OH To 400 mg of Boc-Asp(OBzl)-Ser-Arg(MBS)-Arg(MBS)-Ala-Gln-Asp(OBzl)-Phe-Val-Gln-Trp-Leu-Met(O)-Asn-Thr-OBzl is added 0.25 ml of anisole, followed by addition of 5 ml of methanesulfonic acid. The mixture is stirred at room temperature for 60 minutes, at the end of which time 100 ml of diethyl ether is added, whereupon an oily precipitate is formed. The diethyl ether is discarded by decanting and the residue is dissolved in 10 ml of water. The solution is passed through a column (1×10 cm) of Amberlite IRA-410(acetate-form), the eluate (50 ml) is cooled with ice, 10 ml of 8 N aqueous ammonia is added and the mixture is stirred at 0° C. for 30 minutes, at the end of which time it is lyophilized.

The lyophilizate is dissolved in 30 ml of water and run onto a column (2.2×18 cm) of CMC, and elution is carried out by the linear gradient method with water (500 ml) to 0.2 M aqueous ammonium acetate (500 ml). The fractions from 150 ml through 195 ml are pooled and lyophilized. Yield 150 mg. The lyophilizate is dissolved in 20 ml of water and run onto a column (1.6×5 cm) of Amberlite XAD-2, elution being carried out by the linear gradient method with water (200 ml) to 80% ethanol (200 ml). The fractions from 180 ml through 225 ml are pooled, the ethanol distilled off and the residue lyophilized. Yield 115 mg; $[\alpha]_D^{24} -33.6°(c=0.6,$ 50% aqueous acetic acid); $Rf^3 = 0.54$(Avicel); amino acid analysis (hydrolyzed with 5.7 N-HCl in the presence of 4% thioglycolic acid); Arg. 2.03(2), Trp 0.87(1), Asp 3.03(3), Thr 0.97(1), Ser. 0.73(1), Glu 2.13(2), Ala 1.00(1), Val 1.03(1), Met 1.00(1), Leu 1.03(1), Phe 1.03(1), (peptide content 85.7%).

(16) Production of

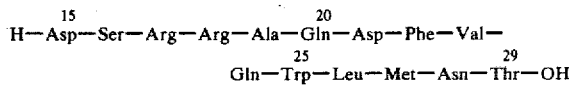

[peptide (I) (15-29)]

In 20 ml of 5% aqueous thioglycolic acid is dissolved 225 mg of H-Asp-Ser-Arg-Arg-Ala-gln-Asp-Phe-Val-Gln-Trp-Leu-Met(O)-Asn-Thr-OH and the solution is allowed to stand at 50° C. for 20 hours, whereupon a gel separates out. The water is distilled off under reduced pressure, the residue is dissolved in 5 ml of 50% aqueous acetic acid and the solution is passed through a column (2.3×118 cm) of Sephadex G-25, elution being carried out with 50% aqueous acetic acid. The fractions from 180 ml through 240 ml are pooled and lyophilized. Yield 220 mg; $[\alpha]_D^{24} -30.0°(c=0.3,$ 50% acetic acid); $Rf^3 = 0.59$(Avicel), amino acid analysis (hydrolyzed with 5.7 N-HCl in the presence of 4% thioglycolic acid); Arg 2.15(2), Trp 0.91(1), Asp 3.13(3), Thr 0.99(1), Ser. 0.87(1), Glu 2.20(2), Ala 1.05(1), Val 0.96(1), Met 1.00(1), Leu 1.07(1), Phe 1.07(1), (peptide content 79.3%).

EXAMPLE 2

Production of

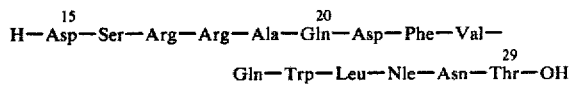

hereinafter referred to as "peptide (II)(15-29)"]

(1) Production of Boc-Nle-Asn-Thr-OBzl

In 30 ml of TFA is dissolved 3.10 g of Boc-Asn-Thr-OBzl and the solution is shaken at room temperature for 10 minutes, at the end of which time it is concentrated. The concentrate is precipitated with 100 ml of diethyl ether and the resultant powders are collected by filtration and dried. It is then dissolved in 30 ml of DMF, and under ice-cooling, 1.5 ml of TEA and, then, Boc-Nle-ONB(prepared from 1.69 g of Boc-Nle-OH, 1.50 g of HONB and 1.73 g of DCC) are added. The mixture is stirred for 15 hours. The solvent is distilled off under reduced pressure, the residue treated with 50 ml of water and the resultant powders collected by filtration, dried, and washed well with diethyl ether. Yield 3.80 g (96.7%); m.p. 160°-163° C.; $[\alpha]_D^{21.5} = 13.6°(c=0.8,$ DMF); $Rf^1 = 0.58$ Elemental analysis (for $C_{26}H_{40}O_8N_4$): Calcd. C, 58.19; H, 7.51; N, 10.44; Found: C, 58.40; H, 7.60; N, 10.37.

(2) Production of Boc-Leu-Nle-Asn-Thr-OBzl

In 30 ml of TFA is dissolved 3.50 g of Boc-Nle-Asn-Thr-OBzl and the solution is shaken at room temperature for 10 minutes. It is then concentrated and precipitated with 150 ml of diethyl ether. The resultant powders are collected by filtration, dried and dissolved in 30 ml of DMF. Under ice-cooling, 1.2 ml of TEA and, then, Boc-Leu-ONB (prepared from 1.66 g of Boc-Leu-OH, 1.41 g of HONB and 1.63 g of DCC) are added. The mixture is stirred for 15 hours, after which the solvent is distilled off under reduced pressure. The residue is treated with 50 ml of water and the resultant powders are collected by filtration, dried and washed thoroughly with ethyl acetate. Yield 3.60 g (83.8%); m.p. 200°-201° C.; $[\alpha]_D^{21.5} -22.7°$ (c=0.8, DMF); $Rf^1=0.60$.

Elemental analysis (for $C_{32}H_{51}O_9N_5 \cdot \frac{1}{2}H_2O$): Calcd.: C, 58.34; H, 7.96; N, 10.63; Found: C, 58.06; H, 7.99; N, 11.02.

(3) Production of Boc-Gln-Asp(OBzl)-Phe-Val-Gln-Trp-Leu-Nle-Asn-Thr-OBzl

In 20 ml of TFA is dissolved 2.00 g of Boc-Leu-Nle-Asn-Thr-OBzl and the solution is shaken at room temperature for 10 minutes, at the end of which time it is concentrated and treated with 70 ml of ether. The resultant powders are collected by filtration, dried and dissolved in 20 ml of DMF. Then, under ice-cooling, 1.3 ml of TEA is added and the mixture shaken well and treated with 100 ml of diethyl ether. The resultant powders are collected by filtration and dissolved in 40 ml of DMF. To this solution are added 3.00 g of Boc-Gln-Asp(OBzl)-Phe-Val-Gln-Trp-OH and 2.20 of HONB, followed by addition of 1.27 g of DCC under ice-cooling. The mixture is stirred for 48 hours. The solvent is then distilled off under reduced pressure, the residue treated with 50 ml of water and the resultant powders collected by filtration and washed well with aqueous acetonitrile. Yield 3.30 g; m.p. 210°-214° C.(decomp.); $[\alpha]_D^{21.5} -11.8°$(c=0.6, NMP); $Rf^3=0.66$.

Elemental analysis (for $C_{78}H_{106}O_{19}N_{14}$): Calcd.: C, 60.68; H, 6.92; N, 12.73; Found: C, 60.92; H, 7.30; N, 12.76.

(4) Production of

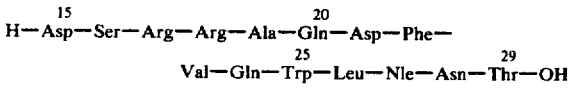

[peptide (II) (15-29)]

To 3.0 g of Boc-Gln-Asp(OBzl)-Phe-Val-Gln-Trp-Leu-Nle-Asn-Thr-OBzl are added 0.2 ml of ethanedithiol and 25 ml of TFA, and after shaking at room temperature for 10 minutes, the mixture is concentrated and treated with diethyl ether. The resultant powders are collected by filtration, dried and dissolved in 15 ml of NMP. The solution is cooled with ice, shaken with 0.8 ml of TEA and treated with diethyl ether. The resultant powders are recovered by filtration and dissolved in 50 ml of DMF, followed by addition of 2.1 g of Boc-Asp(OBzl)-Ser-Arg-(MBS)-Arg(MBS)-Ala-OH and 0.71 g of HONB. After cooling with ice-NAcl, 0.60 g of DCC is added and the mixture is stirred for 24 hours. The precipitated DCU is filtered off, the filtrate concentrated, the residue treated with ethyl acetate and the resultant powders collected by filtration. Yield 3.6 g. To 1.0 g. of the resultant protected peptide is added 1 ml of anisole and, after addition of 10 ml of anhydrous hydrogen fluoride, the mixture is stirred at 0° C. for 60 minutes, at the end of which time it is concentrated under reduced pressure. The concentrate is dissolved in 50 ml of water, washed with diethyl ether and passed through a column (1×10 cm) of Amberlite IRA-410 (acetate-form). The eluate is lyophilized. The lyophilizate is dissovled in 10 ml of 50% acetic acid and run onto a column (2.2×110 cm) of Sephadex LH-20, elution being carried out with 50% acetic acid. The fractions from 125 ml through 180 ml are pooled and lyophilized. The lyophilizate is further dissolved in 50 ml of water and run onto a column (2.2×20 cm) of CMC, elution being carried out by the linear gradient method using 0.005 M aqueous ammonium acetate (500 ml) to 0.2 M aqueous ammonium acetate (500 ml). The fractions from 265 ml through 440 ml are pooled and lyophilized. Yield 145 mg; $[\alpha]_D^{22} -30.9°$(c=0.3, 50% acetic acid); $Rf^3=0.6$(Avicel); amino acid analysis (hydrolyzed with 5.7 N-HCl in the presence of 4% thioglycolic acid: Arg 2.11(2), Trp 0.97(1), Asp 3.40(3), Thr 0.93(1), Ser 0.83(1), Glu 2.10(2), Ala 1.00(1), Val 1.04(1), Leu 0.91(1), Phe 0.84(1), Nle 1.06(1) (peptide content 74%).

EXAMPLE 3

Production of

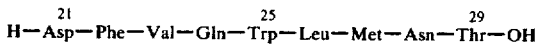

[hereinafter referred to as "Peptide (III) (21-29)"]

In 10 ml of TFA is dissolved 1.0 g of Boc-Leu-Met(0)-Asn-Thr-OBzl and the solution is shaken at room temperature for 10 minutes, after which it is concentrated and treated with 50 ml of diethyl ether. The resultant powders are collected by filtration, dried and dissolved in 10 ml of DMF. Under ice-cooling, the solution is shaken well with 1.1 ml of TEA and, then, treated with 100 ml of diethyl ether. The resultant powders are collected by filtration and dissolved in 20 ml of DMF. To the solution are added 1.33 g of Boc-Asp(OBzl)-Phe-Val-Gln-Trp-OH and 520 mg of HONB, and after cooling with ice, 450 mg of DCC is added and the mixture stirred for 48 hours. The solvent is distilled off under reeduced pressure, 50 ml of water is added to the residue and the resultant powders are collected by filtration and washed with aqueous acetonitrile. Yield 1.72 g. To 1.0 g of this protected peptide is added 0.5 ml of anisol, followed by addition of 10 ml of methanesulfonic acid. The mixture is stirred at room temperature for 10 minutes, after which 100 ml of diethyl ether is added, whereby an oily precipitate separates out. The diethyl ether is decanted off, the residue is dissolved in 20 ml of 30% acetic acid and the solution is passed through a column (1×10 cm) of Amberlite IRA-410(acetate-form) and the effluent is lyophilized. The lyophilizate is dissolved in 5 ml of 50% acetic acid and run onto a column (2.4×110 cm) of Sephadex LH-20, elution being carried out with 50% acetic acid. The fractions from 195 ml through 235 ml are pooled and lyophilized. Yield 550 mg. Of this peptide, 150 mg is taken and dissolved in 5 ml of 50% acetic acid and with the addition of 0.3 ml of thioglycolic acid, reduction is carried out at 45° C. for 16 hours. The reaction mixture is passed through a column (3×135 cm) of Sephadex LH-20, elution being carried out with 30% acetic acid. The fractions from 510 ml through 580 ml are combined and lyophilized. Yield 64 mg.; $[\alpha]_D^{23°} -26.0°$(c=0.2, 80% acetic acid); $Rf^3=0.76$(Avicel); amino acid analysis (hydrolyzed with 5.7 N HCl in the presence of 4% thioglycolic acid): Trp 1.07(1), Asp 2.06(2), Thr 0.98(1), Glu 1.06(1), Val 0.97(1), Met 1.00(1), Leu 1.04(1), Phe 1.11(1) (peptide content 73%).

EXAMPLE 4 production of

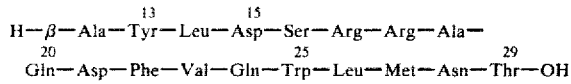

[hereinafter referred to as "Peptide (IV) (13–29)"]
(1) Production of Z-β-Ala-Tyr-Leu-OMe Leu-OMe and the solution is shaken at room temperature for 15 minutes. The solution is concentrated and treated with 100 ml of diethyl ether. The resultant powders are collected by filtration, dried and dissolved in 150 ml of THF. The solution is ice-cooled, 4.0 ml of TEA is added and 8.5 g of Z-β-Ala-ONB is further added. The mixture is stirred for 15 hours, at the end of which time the solvent is distilled off under reduced pressure. The residue is dissolved in 300 ml of ethyl acetate, washed with saturated aqueous sodium hydrogen carbonate (200 ml×3), 10% aqueous citric acid (200 ml×2) and water (200 ml×3) in that order and dried over anhydrous sodium sulfate. The solvent is distilled off, the residue is treated with petroleum ether and the powders collected by filtration and reprecipitated from ethyl acetate-petroleum ether. Yield 10.7 g (83.3%); m.p.112°–113° C.; $[\alpha]_D^{21.5}$ −12.8°(c=0.8, DMF).

Elemental analysis: (for $C_{27}H_{35}O_7N_3$): Calcd.: C, 63.14; H, 6.87; N, 8.18; Found: C, 62.97; H, 6.91; N, 8.09.
(2) Production of Z-β-Ala-Tyr-Leu-OH In 40 ml of methanol is dissolved 5.0 g of Z-β-Ala-Tyr-Leu-OMe and after ice-cooling, 12 ml of 2 N-aqueous sodium hydroxide is added. The mixture is then stirred at room temperature for 90 minutes. The solution is cooled with ice and neutralized with 24 ml of 1 N-HCl. The solvent is then distilled off under reduced pressure. The residue is dissovled in 200 ml of ethyl acetate, rinsed with water (200 ml×2) and dried over anhydrous sodium sulfate. The solvent is distilled off and the resultant crystals are washed with diethyl ether and recovered by filtration. Yield 4.4 g (90.5%; m.p. 144°–145° C.; $[\alpha]_D^{21.5}$ −5.7°(c=0.9, DMF).

Elemental analysis: (for $C_{26}H_{33}O_7N_3$): Calcd.: C, 62.50; H, 6.66; N, 8.41; Found: C, 62.27; H, 6.58; N, 8.82.
(3) Production of

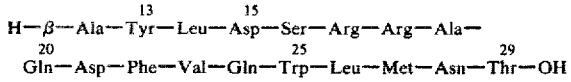

[Peptide (IV)(13–29)]

To 4.6 g of Boc-Asp(OBzl)-Ser-Arg(MBS)-Arg(MBS)-Ala-Gln-Asp(OBzl)-Phe-Val-Gln-Trp-Leu-Met(O)-Asn-Thr-OBzl is added 0.5 ml of anisole, and is added 35 ml of TFA in nitrogen gas stream, and after shaking at room temperature for 15 minutes, the mixture is concentrated and treated with diethyl ether. The resultant powders are collected by filtration and dissolved in 20 ml of NMP. The solution is cooled with ice and shaken well with 0.8 ml of TEA, followed by addition of diethyl ether. The resultant powders are collected by filtration and dissolved in 50 ml of DMF. To this solution are added 0.90 g of Z-β-Ala-Tyr-Leu-OH and 0.64 g of HONB. Under cooling with ice and sodium chloride, 0.55 g of DCC is added and the mixture is stirred for 15 hours. The precipitated DCU is filtered off, the solvent distilled off under reduced pressure and 70 ml of ethyl acetate added to the residue. The resultant powders are collected by filtration. yield 4.3 g. To 1 g. of thus obtained protected peptide is added 1.5 g of anisole, followed by addition of 10 ml of anhydrous hydrogen fluoride. The mixture is stirred at 0° C. for 60 minutes, concentrated and dissolved in 50 ml of water. The solution is washed with 50 ml of diethyl ether. Passed through a column (1×10 cm) of amberlite IRA-410(acetate-form) and lyophilized. The lyophilizate is dissovled in 100 ml of water and run onto a column (2.2×23 cm) of CMC, elution being carried out by the linear gradient method with 0.005 M aqueous ammonium acetate(500 )/0.2 M aqeuous ammonium acetate (500 ml). The fractions from 220 ml through 360 ml are pooled and lyophilized. The lyophilizate is dissolved in 5 ml of 50% acetic acid and passed through a column (2.4×118 cm) of Sephadex LH-20, elution being carried out with 50% acetic acid. The fractions from 130 ml through 166 ml are pooled and lyophilized. Yield 80 mg.

Of this peptide, a 70 mg-portion is dissolved in 7 ml of 50% acetic acid and after addition of 0.35 ml of thioglycolic acid, the solution is allowed to stand at 45° C. for 12 hours. After 0.35 ml of thioglycolic acid is further added, the solution is allowed to stand 45° C. for 24 hours, whereby the reaction is completed. The reaction mixture is passed through a column (2.4×120 cm) of Sephadex G-25, elution being carried out with 50% acetic acid. The fractions from 160 ml through 220 ml are pooled and lyophilized. Yield 66 mg; $[\alpha]_D^{21.5}$ −29.3°(c=0.4, 50% acetic acid); $Rf^3$=0.61 (Avicel); amino acid analysis (hydrolyzed with 5.7 N HCl in the presence of 4% thioglycolic acid): Arg 2.19(2), Trp 0.92(1), Asp 3.44(3), Thr 0.91(1), Ser 0.69(1), Glu 2.32(2), Ala 1.12(1), Val 1.14(1), Met 1.00(1), Leu 2.02(2), Tyr 1.05(1), Phe 1.05(1), βAla 1.13(1) (peptide content 81%).

REFERENCE EXAMPLE 1

Production of peptide (I) (15–29)-BSA conjugate (1)

In 4 ml of 0.2 M phosphate buffer (pH 7.3) are dissolved 10 mg of peptide (I)(15–29) prepared according to Example 1 and 20 mg of BSA. To this solution is added 4 ml of a 5% aqueous solution of GLA and the mixture is stirred at room temperature for 3 hours, after which it is dialyzed (2l of water×4) at 4° C. and lyophilized to obtain the above-indicated conjugate. yield 38 mg.

REFERENCE EXAMPLE 2

Production of peptide (I) (15–29)-BSA conjugate (2)

To 10 ml of a 0.2% aqueous solution of BSA are added solid of succinic anhydride (2 mg) in small increments and the reaction is carried out while the pH is maintained at pH 7.0 to 8.0 with 0.1 N-NaOH, whereby the BSA is succinylated. After the reaction has been completed, the reaction mixture is dialyzed (2 l of water×4) at 4° C. and lyophilized. To this succinylated BSA is added 10 mg of the peptide (I) (15–29) according to Example 1 and the mixture dissolved in 10 ml of 0.05 M phosphate buffer (pH 6.5). Then 10 mg of ECDI is gradually added and the reaction is carried out at 4° C. for 2 days, with gentle stirring. After the reaction has been completed, the reaction mixture is dialyzed (2 l of water×4) and lyophilized to obtain the above-indicated conjugate. Yield 39 mg.

REFERENCE EXAMPLE 3

Production of peptide (IV)(13-29)-BSA conjugate

The procedure of Reference Example 1 is repeated except that 10 mg of peptide (IV)(13-29) is used in lieu of 10 mg of peptide (I)(15-29) to obtain the above-indicated BSA conjugate. Yield 39 mg.

REFERENCE EXAMPLE 4

Method for producing the antibody.

In 1 ml of physiological saline is dissolved 2 mg of the conjugate of BSA with the peptide prepared in the same manner as Reference Example 1, 2 or 3 and the solution is mixed well with 1 ml of Freund's complete adjuvant. The resulting emulsion is injected intramuscularly into both thighs and subcutaneously at multiple sites along the dorsal surface of a rabbit. The above procedure is repeated 5 times at intervals of 2 weeks and a blood sample is taken a week after the final immunization for a pilot assay. By the above procedure is obtained a glucagon antibody which does not react with pancreatic glucagon and which is used as a one hundred thousand-fold to five hundred thousand-fold dilution.

EXAMPLE 5

Production of peptide (I)(15-29)-β-D-galactosidase conjugate

In 2 ml of 0.1 M phosphate buffer (pH 6.3) is suspended 2 mg of the peptide (I) (15-29) obtained in Example 1, followed by addition of 0.5 ml of a 0.5% solution of m-MBHS in THF. The reaction is carried out at 30° C. for half an hour. The reaction mixture is passed through a column (0.9×53 cm) of Sephadex G-25 equilibrated with 0.1 M phosphate buffer to separate the maleimidated peptide fraction from the excess reagent. To 1 ml of thus obtained maleimidated peptide fraction is added 0.1 ml of β-D-galactosidase solution (5 mg/ml) and the reaction is carried out at room temperature for 2 hours, with occasional shaking. After the reaction has been completed, the mixture is purified by Sepharose 6 B column chromatography with 0.01 M phosphate buffer (pH 7.0) containing 0.1% BSA, 0.1% $NaN_3$, 0.1 M NaCl and 1 mM $MgCl_2$. The enzymatically active fraction is thus separated to recover the peptide-enzymne conjugate.

Properties of this conjugate are as follows.

(1) This conjugate decomposes o-nitrophenyl-β-D-galactopyranoside and 4-methylumbelliferyl-β-D-galactopyranoside, which are synthetic substrates for EIA, to liberate 0-nitrophenol and 4-methylumbelliferone, respectively.

(2) The optimal pH for enzymatic activity is 7.0 to 7.7.

(3) More than about 90 percent of this enzymatically active conjugate is reactive to anti-pancreatic glucagon antibody, and its immunologic activity as well as enzymatic activity is stable under refrigerator conditions for more than 6 months.

(4) The conjugate has a molecular weight of about five hundred and fifty thousand with the molar ratio of peptide (I) to enzyme being about 7.

(5) The conjugate is readily soluble in aqueous solvents between pH 5 and pH 9.

Figure 2:
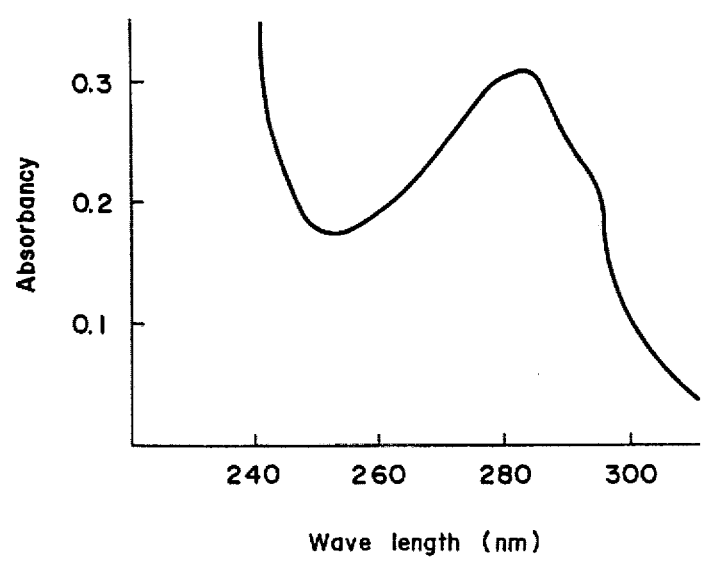

(6) For the ultraviolet absorption spectrum of the conjugate, reference is made to FIG. 2. λmax=283 nm.

(7) For the amino acid analysis of the conjugate, reference is made to Table 5.

(8) Other properties of the conjugate are similar to those of β-D-galactosidase ]Boyer: The enzymes, Vol. 7 (1972), p. 617, Academic Press, New York-London]

EXAMPLE 6

Production of peptide (II)(15-29)-β-D-galactosidase conjugate

The procedure of Example 5 is repeated except that 2 mg of the peptide (II) according to Example 2 is used in lieu of 2 mg of peptide (I)(15-29) to obtain a peptide-β-D-galactosidase conjugate.

Except for the following properties (3 and 4), properties of this conjugate are similar to those [(1),(2),(5),(6) and (8)] of the conjugate according to Example 5.

(3) More than about 80 percent of this enzymatically active conjugate is reactive to anti-PG antibody, and its immunologic activity as well as enzymatic activity is stable under refrigerator conditions for more than 6 months.

(4) This conjugate has a molecular weight of about five hundred and fifty thousand, the molar ratio of peptide (II) to enzyme being about 6.

EXAMPLE 7

Production of peptide (III)(21-29)-β-D-galactosidase conjugate

The procedure of Example 5 is repeated except that 1.2 mg of the peptide (III)(21-29) according to Example 3 is used in lieu of 2 mg of peptide (I)(15-29) to obtain a peptide-β-D-galactosidase conjugate.

Except for the following property (4), properties of this conjugate are similar to those [(1),(2),(3),(5),(6) and (8)] of the conjugate according to Example 5.

(4) This conjugate has a molecular weight of about five hundred and fifty thousand, the molar ratio of peptide (III) to enzyme being about 8.

EXAMPLE 8

Production of peptide (IV)(13-29)-β-D-galactosidase conjugate

The procedure of Example 5 is repeated except that 2.4 mg of peptide (IV)(13-29) according to Example 4 is used in lieu of 2 mg of peptide (I)(15-29) to obtain a peptide-β-D-galactosidase conjugate.

Except for the following properties (3),(4) and (7), properties of this conjugate are similar to those [(1),(2),(5),(6) and (8)] of the conjugate according to Example 5.

(3) More than about 75 percent of this enzymatically active conjugate is reactive to anti-pancreatic glucagon antibody and its immunologic activity as well as enzymatic activity is stable under refrigerator conditions for more than 6 months.

(4) This conjugate has a molecular weight of about five hundred and fifty thousand, the molar ratio of peptide (IV) to enzyme being about 5.

(7) For the amino acid analysis of this conjugate, reference is made to Table 6.

EXAMPLE 9

Production of peptide (I)(15-29)-alkaline phosphatase conjugate.

On the one hand, 0.2 ml of a suspension of alkaline phosphates (5 mg/ml) is centrifuged and the resultant sediment is dissolved in 0.1 ml of 0.1 M phosphate buffer (pH 6.8). On the other hand, 1 mg of peptide (I)(15–29) according to Example 1 is dissolved in 1 ml of the same buffer as above, and the above enzyme solution is added. Then, 0.1 ml of 2% GLA solution is added and the reaction is carried out at room temperature for 2 hours, at the end of which time the reaction mixture is dialyzed against the same phosphate buffer at about 5° C. overnight. The dialysate is further purified by Sephadex G100 column chromatography with phosphate buffer (pH 6.8) containing 0.1 M NaCl. The enzymatically active fractions are pooled to recover a peptide-enzyme conjugate.

Properties of the above conjugate are as follows.

(1) This conjugate decomposes phenyl phosphate and p-nitrophenyl phosphate, which are synthetic substrates for EIA, to yield phenol and p-nitrophenol, respectively.

(2) The optimal pH for enzymatic activity is 9.5 to 10.5.

(3) More than 90 percent of this enzymatically active conjugate is reactive to anti-pancreatic glucagon antibody, and its immunologic activity as well as enzymatic activity is stable under refrigerator conditions for more than 3 months.

(4) This conjugate has a molecular weight of about one hundred and forty thousand, the molar ratio of peptide (I) to enzyme being about 20.

(5) This conjugate is readily soluble in aqueous solvents between pH 6 and pH 11.

Figure 3:
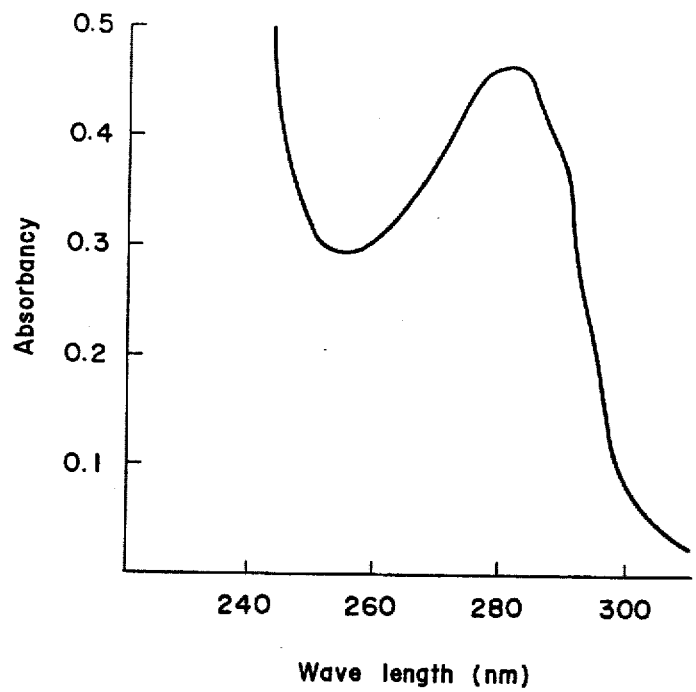

(6) For the ultraviolet absorption spectrum of this conjugate, reference is made to FIG. 3. λmax=281 nm.

(7) For its amino acid analysis, reference is made to Table 7.

(8) Other properties are similar to those of alkaline phosphatase [Boyer: The Enzymes, Vol. 4 (1971), p. 417, academic Press, New York-London]

EXAMPLE 10

Production of peptide (II)(15–29)-alkaline phosphates conjugate

The procedure of Example 9 is repeated except that 1 mg of peptide (II)(15–29) according to Example 2 is used in lieu of 1 mg of peptide (I) (15–29) to obtain a peptide-alkaline phosphatase conjugate.

Except for the following property (4), properties of this conjugate are similar to those [(1),(2),(3),(5),(6) and (8)] described in Example 9.

(4) This conjugate has a molecular weight of about one hundred and forty thousand, the molar ratio of peptide (II) to enzyme being about 20.

EXAMPLE 11

Production of peptide (III) (21–29)-alkaline phosphatase conjugate

The procedure of Example 9 is repeated except that 0.6 mg of peptide (III)(21–29) according to Example 3 is used in lieu of 1 mg of peptide (I)(15–29) to obtain a peptide-alkaline phosphatase conjugate.

Except for the following property (4), properties of this conjugate are similar to those [(1),(2),(3),(5),(6) and (8)] of the conjugate according to Example 9.

(4) This conjugate has a molecular weight of about one hundred and thirty thousand, the molar ratio of peptide (III) to enzyme being about 23.

EXAMPLE 12

Production of peptide (IV)(13–29)-alkaline phosphatase conjugate

The procedure of EXAMPLE 9 is repeated except that 1.2 mg of peptide (IV)(13–29) according to Example 4 is used in lieu of 1 mg of peptide (I)(15–29) to obtain a peptide-alkaline phosphatase conjugate.

Except for the following properties (4) and (7), properties of this conjugate are similar to those [(1), (2),(3),(5),(6) and (8)] of the conjugate according to Example 9.

(4) This conjugate has a molecular weight of about one hundred and forty thousand, the molar ratio of peptide (IV) to enzyme being about 16.

(7) For the amino acid analysis of this enzyme, reference is made to Table 8.

REFERENCE EXAMPLE 5

Production of pancreatic glucagon (1–29)-β-D-galactosidase conjugate

The procedure of Example 5 is repeated except that 4 mg of pancreatic glucagon (1–29) is used in lieu of 2 mg of peptide (I)(15–29) to obtain a peptide-β-D-galactosidase conjugate.

Except for the following properties [(3) and (4)], properties of this conjugate are similar to those [(1),(2),(5),(6) and (8)] of the conjugate according to Example 5.

(3) More than about 65 percent of this conjugate is reactive to anti-pancreatic glucagon antibody, and its immunologic activity as well as enzymatic activity is stable under refrigerator conditons for more than 3 months.

(4) This conjugate has a molecular weight of about five hundred and fifty thousand, the molar ratio of pancreatic glucagon to enzyme being about 3.

REFERENCE EXAMPLE 6

Production of pancreatic glucagon (1–29)-alkaline phosphatase conjugate

The procedure of Example 9 is repeated except that 2 mg of pancreatic glucagon (1–29) is used in lieu of 1 mg of peptide (I)(15–29) to obtain a peptide-alkaline phosphatase conjugate.

Except for the following property (4), properties [(1), (2),(3),(5),(6) and (8)] of this conjugate are similar to those [(1),(2),(3),(5),(6) and (8)] of the conjugate according to Example 5.

(4) This conjugate has a molecular weight of about one hundred and fifty thousand, the molar ratio of pancreatic glucagon to enzyme being about 13.

EXAMPLE 13

In a preliminary test, samples containing various dilutions of antiserum [0.2 ml of buffer, 0.1 ml of peptide-β-D-galactosidase complex and 0.1 ml of anti-serum (one hundred through one million-fold diluted) are prepared for each of 30K, N16a and N6c antisera and each sample is allowed to stand at 5° C. for 24 hours, whereby the enzymatically active fraction of each peptide-β-D-galactosidase conjugate [of a suitable predetermined concentration (ca. 10 μU/ml)] is bound to the antiserum. Then, 0.1 ml of antirabbit IgG serum (a 10-fold dilution of commercial antiserum) and 0.1 ml of buffer containing 1% of normal rabbit serum are added. The resultant mixture is allowed to stand at 5° C. overnight and centrifuged. The sediment is washed and suspended in 0.5 ml of a substrate solution [20 μg/ml of 4-methylumbelliferyl-β-D-galactopyranoside as dissolved in 0.01 M phosphate buffer (pH 7.0) containing 0.1% BSA, 0.1% NaN₃, 0.1 M NaCl and 1 mM MgCl₂]. The reaction is conducted at 37° C. for 2 hours. After the reaction has been completed, the fluoroscence intensity of the 4-methylumbelliferone liberated by enzymatic cleavage is measured at an excitation wavelength of 365 nm and a fluorescence wavelength of 450 nm.

Then, for a quantitative assay of pancreatic glucagon in a test fluid, 0.1 ml each of the antiserum of the dilution factor determined as above and the peptide-$\beta$-D-galactosidase conjugate are added to a mixture of 0.1 ml of the test fluid and 0.1 ml of buffer solution. Thereafter, the same assay procedure as described above is follows.

The results are set forth in Tables 1 through 3.

It will be apparent from Table 1 that when used in combination with the peptide (I)- or peptide (II)-enzyme conjugate, 30K antiserum gives estimates with a markedly improved sensitivity as compared with the assay using the same antiserum in combination with the conventional PG-enzyme conjugate in a homologous system.

Similarly, antisera N16a (Table 2) and N6c (Table 3) also give improved sensitivities at low concentrations of pancreatic glucagon particularly when used in combination with the peptide (II)- or peptide (III)-enzyme conjugate in a heterologous assay system according to this invention.

It will be seen that very high sensitivities are obtained in the enzyme immunoassay of pancreatic glucagon when the conjugate of a labeling enzyme with a peptide different from the peptide used for the preparation of an assay PG antibody is used in combination with said antibody (i.e. in a heterologous assay system).

TABLE 1

| The peptide used in the preparation of antiserum | Pancreatic glucagon (1-29) | | | | |
|---|---|---|---|---|---|
| Antiserum | 30 K[3] | | | | |
| Final dilution of antiserum | Fifty thousand-fold diluted | | | | |
| The peptide used in the preparation of peptide-enzyme conjugate[1] | PG (1-29) | Peptide(IV) (13-29) | Peptide(I) (15-29) | Peptide(II) (15-29) | Peptide(III) (21-29) |
| Coupling of antiserum and peptide-enzyme conjugate | Homologous | Heterologous | Heterologous | Heterologous | Heterologous |
| B/Bo[2] (%) Concentration of pancreatic glucagon (pg/ml) | | | | | |
| 0 | 100 | 100 | 100 | 100 | 100 |
| 100 | 80 | 71 | 68 | 50 | 78 |
| 500 | 63 | 41 | 30 | 30 | 44 |

[1]$\beta$-D-Galactosidase was used as the enzyme.
[2]B:The enzymatic activity bound to a solid phase in the presence of PG.
Bo:The enzymatic activity bound to a solid phase in the absence of PG.
[3]Purchased from the University of Texas through Japan Isotope Association.
Literature:Diabetes, Vol.17 (1968), p.321

TABLE 2

| The peptide used in the preparation of antiserum | Peptide (IV) (13-29) | | | | |
|---|---|---|---|---|---|
| Antiserum | N16a[3] | | | | |
| Final dilution of antiserum | Two hundred thousand-fold diluted | | | | |
| The peptide used in the preparation of peptide-enzyme conjugate[1] | PG (1-29) | Peptide(IV) (13-29) | Peptide(I) (15-29) | Peptide(II) (15-29) | Peptide(III) (21-29) |
| Coupling of antiserum and peptide-enzyme conjugate | Heterologous | Homologous | Heterologous | Heterologous | Heterologous |
| B/Bo[2] (%) Concentration of pancreatic glucagon (pg/ml) | | | | | |
| 0 | 100 | 100 | 100 | 100 | 100 |
| 100 | 100 | 101 | 98 | 83 | 81 |
| 500 | 79 | 81 | 80 | 63 | 59 |

[1] and [2] are as defined hereinbefore
[3]See Reference Examples 3 and 4.

TABLE 3

| The peptide used in the preparation of antiserum | Peptide (I) (15-29) | | | | |
|---|---|---|---|---|---|
| Antiserum | N6c[3] | | | | |
| Final dilution of antiserum | Four hundred thousand-fold diluted | | | | |
| The peptide used in the preparation of peptide enzyme conjugate[1] | PG (1-29) | Peptide(IV) (13-29) | Peptide(I) (15-29) | Peptide(II) (15-29) | Peptide(III) (21-29) |
| Coupling of antiserum and peptide-enzyme | | | | | |

TABLE 3-continued

| conjugate B/Bo[2] (%) | Concentration of pancreatic glucagon (pg/ml) | Heterologous | Heterologous | Homologous | Heterologous | Heterologous |
|---|---|---|---|---|---|---|
| | 0 | 100 | 100 | 100 | 100 | 100 |
| | 100 | 100 | 102 | 104 | 78 | 80 |
| | 500 | 79 | 75 | 80 | 54 | 60 |

[1] and [2] are as defined hereinbefore.
[3] See Reference Examples 1 and 4.

EXAMPLE 14

The plasma PG titers of several species of rats are determined by the above-described enzyme immunoassay procedure with the use of 30K antiserum and peptide (I)(15–29)-$\beta$-D-galactosidase conjugate and the results are compared with the results of the conventional radioimmunoassays with the same 30K antiserum.

The results are shown in Table 4.

As shown in Table 4, the EIA method of this invention for a quantitative determination of pancreatic glucagon produced results in good agreement with the results of the conventional RIA using 30K antiserum which is regarded as one of the most reliable assay procedure. It is thus evident that the EIA method of this invention permits a quick determination of PG in various plasma samples with high sensitivity and reliability.

TABLE 4

| Test plasma | Concentration of PG(ng/ml) | |
|---|---|---|
| | EIA | RIA |
| 1 | 0.42 | 0.50 |
| 2 | 0.27 | 0.23 |
| 3 | 0.27 | 0.28 |
| 4 | 0.64 | 0.57 |
| 5 | 0.39 | 0.42 |
| 6 | 0.40 | 0.47 |

EXAMPLE 15

In the same manner as Example 13, samples containing various dilutions of 30K antiserum [0.2 ml of buffer, 0.1 ml of peptide (I)-alkaline phosphatase conjugate or peptide (II)-alkaline phosphatase conjugate and 0.1 ml of antiserum (one hundred to one hundred thousand-fold diluted)] are allowed to stand at 5° C. for 24 hours, whereby the enzymatically active fraction of each peptide-alkaline phosphatase conjugate [with a predetermined suitable concentration (about 4 mU/ml)] is coupled to the antiserum. Then, 0.1 ml of anti-rabbit IgG serum (a 10-fold dilution of commercial antiserum) and 0.1 ml of buffer containing 1% of normal rabbit serum are added and the resulting mixture is allowed to stand at 5° C. overnight. The mixture is then centrifuged and the sediment washed and suspended in 0.5 ml of a substrate solution [2 mg/ml of p-nitrophenyl phosphate as dissolved in 0.05 M sodium carbonate buffer (pH 9.8) containing 1 mM MgCl$_2$). The reaction is allowed to proceed at 37° C. overnight. After the reaction is completed, the absorption intensity of p-nitrophenol as liberated by enzymatic cleavage is measured at 405 nm.

Then, for an assay of PG in a test fluid, 0.1 ml each of the 30K antiserum at the above predetermined dilution and the peptide-alkaline phosphatase conjugate are added to a mixture of 0.1 ml of the test fluid and 0.1 ml of buffer. Thereafter, the above-described assay procedure is followed. The assay results are presented in FIG. 1.

In FIG. 1, —.— represents results for the peptide (I)-enzyme conjugate; ----X---- represents results for the peptide (II)-enzyme conjugate; and —O— represents results for PG-enzyme conjugate.

FIG. 1 is the standard curve for pancreatic glucagon.

30K antiserum gives the maximal sensitivity when used in combination with the peptide (I)-alkaline phosphatase conjugate according to Example 9 (heterologous assay system), while the conventional homologous assay system involving the use of PG-alkaline phosphatase conjugate gives only a low sensitivity.

TABLE 5

| Amino acid | Peptide (I)-$\beta$-D-galactosidase conjugate |
|---|---|
| Lys (lysine) | 50 |
| His (histidine) | 42 |
| Arg | 115 |
| Asp | 166 |
| Thr | 78 |
| Ser | 77 |
| Glu | 158 |
| Pro (proline) | 93 |
| Gly (glycine) | 100 |
| Ala | 102 |
| Val | 82 |
| Met | 18 |
| Ile (isoleucine) | 53 |
| Leu | 123 |
| Tyr | 35 |
| Phe | 54 |
| $\beta$-Ala | — |

(Note)
The number of mols of each amino acid per 100 mols of glycine.

TABLE 6

| Amino acid | Peptide (IV)-$\beta$-D-galactosidase conjugate |
|---|---|
| Lys (lysine) | 57 |
| His (histidine) | 34 |
| Arg | 120 |
| Asp | 177 |
| Thr | 80 |
| Ser | 80 |
| Glu | 158 |
| Pro (proline) | 91 |
| Gly (glycine) | 100 |
| Ala | 116 |
| Val | 77 |
| Met | 16 |
| Ile (isoleucine) | 51 |
| Leu | 128 |
| Tyr | 32 |
| Phe | 51 |
| $\beta$-Ala | — |

(Note)
The number of mols of each amino acid per 100 mols of glycine.

TABLE 7

| Amino acid | Peptide (I)-alkaline phosphatase conjugate |
| --- | --- |
| Lys (lysine) | 49 |
| His (histidine) | 19 |
| Arg | 81 |
| Asp | 138 |
| Thr | 92 |
| Ser | 80 |
| Glu | 132 |
| Pro (proline) | 66 |
| Gly (glycine) | 100 |
| Ala | 116 |
| Val | 88 |
| Met | — |
| Ile (isoleucine) | 34 |
| Leu | 89 |
| Tyr | — |
| Phe | 40 |
| β-Ala | — |

(Note)
The number of mols of each amino acid per 100 mols of glycine.

TABLE 8

| Amino acid | Peptide (IV)-alkaline phosphatase conjugate |
| --- | --- |
| Lys (lysine) | 54 |
| His (histidine) | 13 |
| Arg | 73 |
| Asp | 137 |
| Thr | 92 |
| Ser | 84 |
| Glu | 132 |
| Pro (proline) | 68 |
| Gly (glycine) | 100 |
| Ala | 117 |
| Val | 90 |
| Met | — |
| Ile (isoleucine) | 36 |
| Leu | 99 |
| Tyr | — |
| Phe | 39 |
| β-Ala | 8 |

(Note)
The number of mols of each animo acid per 100 mols of glycine.

EXAMPLE 16

In a preliminary test, a mixture comprised of 100 μl of a varying dilution of one of various antisera (30K, G21, G7, R517 and N6E), 100 μl of peptide-β-D-galactosidase conjugate, 50 μl of Antagosan (Hoechst, ten thousand units/ml) and 250 μl of assay buffer [0.02 M phosphate buffer (pH 7.3) containing 0.5% HSA, 0.5% EDTA, 0.1% NaN₃ and 0.1 M NaCl] is maintained at 5° C. for 96 hours, whereby the enzymatically active fraction of the corresponding peptide-β-D-galactosidase conjugate (which has a predetermined suitable enzymatic activity (about 10 μU/ml)] is bound to the antiserum. Then, 100 μl of a suspension of 5% anti-rabbit IgG antibody-cellulose complex is added and the reaction is carried out at 30° C. for 4 hours. This mixture is centrifuged and the sediment is washed and suspended in 500 μl of substrate solution [20 μg/ml of 4-methylumbelliferyl-β-D-galactopyranoside as dissolved in 0.01 M phosphate buffer (pH 7.0) containing 0.1% BSA, 0.1% NaN₃, 0.1M NaCl and 1 mM MgCl₂]. The reaction is carried out at room temperature overnight. After the reaction has been completed, the fluorescence intensity of 4-methylumbelliferone as liberated by enzymatic cleavage was measured at an excitation wavelength of 365 nm and a fluorescence wavelength of 450 nm.

Then, for an assay of PG in the test fluid, 100 μl each of the above predetermined dilution of antiserum and the peptide-β-D-galactosidase conjugate are added to a mixture of 50 μl of the test fluid, 50 μl of Antagosan and 200 μl of assay buffer. Thereafter, the same assay procedure as above is followed.

Figure 4:
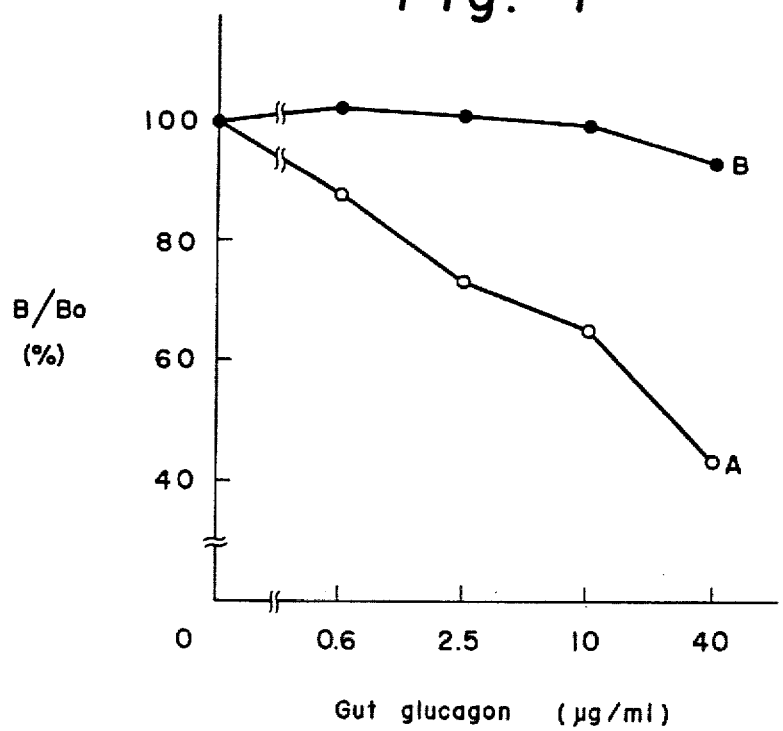
Figure 5:
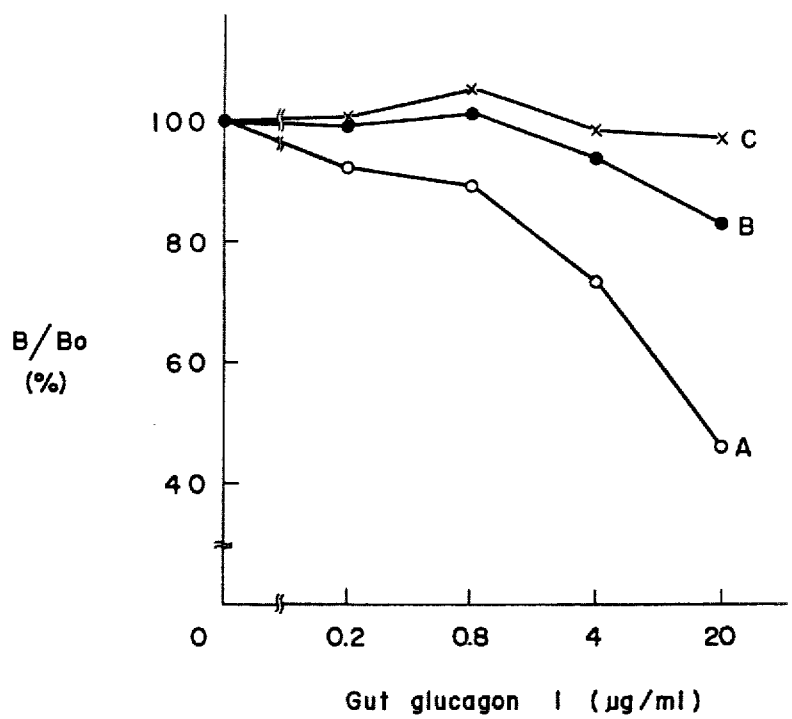
Figure 6:
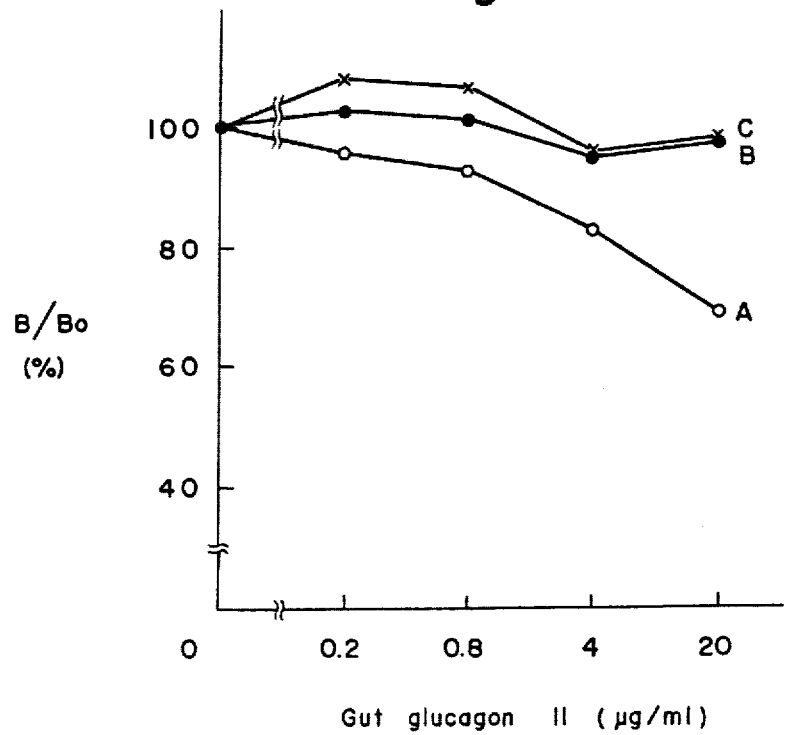

The results of assays are presented in FIGS. 4 through 6.

In FIGS. 4 to 6, —.—represents results for the peptide (I)-enzyme conjugate, ----X---- represents results for the peptide (III)-enzyme conjugate; and—o—represents results for PG-enzyme conjugate.

Referring to FIG. 4, the antiserum R517 obtained by immunizing a rabbit with PG was reacted with the gut glucagon extracted from the small intestinal mucosa of a dog. The above antiserum shows a competitive binding affinity with gut glucagon when used in combination with a conjugate of PG itself (hereinafter referred to as "PG(1-29)" with enzyme but fails to show any significant competitive binding affinity, even with respect to a high concentration of gut glucagon, when used in combination with peptide (I)(15-29)-enzyme conjugate. It is therefore clear that the assay system involving the use of R517 antiserum and peptide (I)-enzyme conjugate is specific to pancreatic glucagon.

In the cases represented by FIGS. 5 and 6, the antiserum G7 obtained by immunizing a rabbit with pancreatic glucagon was reacted with gut glucagon. Here, the above mentioned extract of the canine small-intestinal mucosa is further purified by gel-filtration column chromatography on Sephadex G50 and the resultant two gut glucagons with dissimilar molecular weights [I: estimated mol. wt. about 10,000; II: estimated mol. wt. about 2,000 to 4,000][Hormone and Metabolic Research, Vol. 8, p. 170(1976)] are employed in the study of the cross-reactivity of the above antiserum with gut glucagon. The use of antiserum in combination with peptide (I) (15-29)-enzyme conjugate or peptide (III) (21-29)-enzyme conjugate does not show as great a competitive binding reaction with any of the two gut glucagons as that observed when the same antiserum was used in combination with PG(1-29)-enzyme conjugate. Thus, G7 PG-nonspecific antiserum, like R517 antiserum, becomes apparently specific to PG when it is used in combination with the peptide (I)-enzyme or peptide (III)-enzyme conjugate.

EXAMPLE 17

Human plasma is previously fractionated by gel-filtration column chromatography into big plasma glucagon (hereinafter referred to as "BPG") and pancreatic glucagon (PG) fractions, and by the procedure described in Example 16, PG levels are determined. The results are compared with the results of the conventional enzyme immunoassay with PG antiserum and PG(1-29)-enzyme conjugate.

These results are given in Table 9. It will be apparent from Table 9 that the heterologous assay system according to this invention does not reveal any significant deviation of results for the PG fraction but gave very low PG levels for the PG fraction. Thus, it is clear that so far as the antisera 30K and G21 obtained by immunizing rabbits with PG are concerned, the use of such sera in combination with peptide (I)(15-29)-enzyme conjugate results in a reduction in the competitive binding reaction with BPG or in the degree of inhibitory effect of BPG on the antigen-antibody reaction, thus enabling one to determine the PG level in plasma more specifically than by an assay with the use of PG(1-29)-enzyme conjugate. When the N6E antiserum obtained by immunizing a rabbit with peptide (I)(15≧29) is used in combination with peptide (III)(21-29)-enzyme conjugate, the BPG fraction yields a still lower PG value showing that the assay system is still more specific to pancreatic glucagon.

TABLE 9

| The peptide used in the preparation of antiserum | | PG (1-29) | | Peptide(II)(15-29) |
|---|---|---|---|---|
| Antiserum | 30 K[3] | | G21[4] | N6E[5] |
| The peptide used in the preparation of peptide-enzyme conjugate[1] | PG | Peptide I | PG | Peptide I | Peptide (III) (21-29) |
| Coupling of antiserum and peptide-enzyme conjugate | Homologous | Heterologous | Homologous | Heterologous | Heterologous |
| Plasma Fraction[2] | | | Glucagon immunoreactivity (pg/ml)[6] | | |
| 1  BPG | 4,100 | 1,080 | 3,200 | 920 | 870 |
|    PG  | 310 | 290 | 310 | 280 | 420 |
| 2  BPG | 550 | 430 | 1,030 | 630 | 360 |
|    PG  | 106 | 88 | 103 | 78 | 78 |
| 3  BPG | 360 | 260 | 410 | 270 | 243 |
|    PG  | 94 | 64 | 110 | 105 | 76 |

[1] $\beta$-D-Galactosidase was used as the enzyme.
[2] Plasma is purified with a column packed with Sephadex G-50.
BPG: Big plasma glucagon
PG: Pancreatic glucagon
[3] Literature: Diabetes Vol.17, p.321 (1968)
[4] Literature: Diabetes Vol.18, p.1 (1969)
[5] Reference Example 4
[6] The quantity equivalent to pancreatic glucagon.

What we claim is:

1. A peptide-enzyme conjugate obtained by coupling a reactive substituent group of a labeling enzyme and of a peptide of the formula:

H-R$_1$-Phe-Val-Gln-Trp-Leu-R$_2$-Asn-Thr-OH wherein R$_1$ is a peptide fragment selected from the group consisting of Asp, Gln-Asp, Ala-Gln-Asp, Arg-Ala-Gln-Asp, Arg-Arg-Ala-Gln-Asp, Ser-Arg-Arg-Ala-Gln-Asp, Asp-Ser-Arg-Arg-Ala-Gln-Asp, Leu-Asp-Ser-Arg-Arg-Ala-Gln-Asp, Tyr-Leu-Asp-Ser-Arg-Arg-Ala-Gln-Asp and $\beta$-Ala-Tyr-Leu-Asp-Ser-Arg-Arg-Ala-Gln-Asp, and wherein R$_2$ is Met or Nle.

2. The peptide-enzyme conjugate as claimed in claim 1, wherein the labeling enzyme is $\beta$-galactosidase or alkaline phosphatase.

3. The peptide-enzyme conjugate as claimed in claim 2, wherein the conjugate is one obtained by coupling $\beta$-D-galactosidase with a peptide of the formula:

H-Asp-Ser-Arg-Arg-Ala-Gln-Asp-Phe-Val-Gln-Trp-Leu-Nle-Asn-Thr-OH.

4. The peptide-enzyme conjugate as claimed in claim 2, wherein the conjugate is one obtained by coupling $\beta$-D-galactosidase with a peptide of the formula:

$\beta$-Ala-Tyr-Leu-Asp-Ser-Arg-Arg-Ala-Gln-Asp-Phe-Val-Gln-Trp-Leu-Met-Asn-Thr-OH.

5. The peptide-enzyme conjugate as claimed in claim 2, wherein the conjugate is one obtained by coupling alkaline phosphatase with a peptide of the formula:

H-Asp-Ser-Arg-Arg-Ala-Gln-Asp-Phe-Val-Gln-Trp-Leu-Nle-Asn-Thr-OH.

6. The peptide-enzyme conjugate as claimed in claim 2, wherein the conjugate is one obtained by coupling alkaline phosphatase with a peptide of the formula:

$\beta$-Ala-Tyr-Leu-Asp-Ser-Arg-Arg-Ala-Gln-Asp-Phe-Val-Gln-Trp-Leu-Met-Asn-Thr-OH.

7. A method of enzyme immunoassay of pancreatic glucagon which comprises reacting a peptide-enzyme conjugate obtained by coupling a reactive substituent group of labeling enzyme and of a peptide of the formula:

H-R$_1$-Phe-Val-Gln-Trp-Leu-R$_2$-Asn-Thr-OH wherein R$_1$ is a peptide fragment selected from the group consisting of Asp, Gln-Asp, Ala-Gln-Asp, Arg-Ala-Gln-Asp, Arg-Arg-Ala-Gln-Asp, Ser-Arg-Arg-Ala-Gln-Asp, Asp-Ser-Arg-Arg-Ala-Gln-Asp, Leu-Asp-Ser-Arg-Arg-Ala-Gln-Asp, Tyr-Leu-Asp-Ser-Arg-Arg-Ala-Gln-Asp and $\beta$-Ala-Tyr-Leu-Asp-Ser-Arg-Arg-Ala-Gln-Asp, and wherein R$_2$ is Met or Nle, a test fluid, a plasma and an anti-glucagon antibody competitively and measuring the amount of pancreatic glucagon in the test fluid by detecting the enzyme activity in the liquid or solid phase.

8. The method as claimed in claim 7, wherein the labeling enzyme is $\beta$-D-galactosidase or alkaline phosphatase.

9. A peptide-enzyme conjugate obtained by coupling a reactive substituent group of a labelling enzyme and of a peptide of the formula:

H-R$_3$-Phe-Val-Gln-Trp-Leu-Met-Asn-Thr-OH wherein R$_3$ is a peptide fragment selected from the group consisting of Asp, Gln-Asp, Ala-Gln-Asp, Arg-Ala-Gln-Asp, Arg-Arg-Ala-Gln-Asp, Ser-Arg-Arg-Ala-Gln-Asp, and Asp-Ser-Arg-Ala-Gln-Asp.

10. The peptide-enzyme conjugate as claimed in claim 9, wherein the labeling enzyme is $\beta$-galactosidase or alkaline phosphatase.

11. The peptide-enzyme conjugate as claimed in claim 9, wherein the conjugate is one obtained by coupling a labeling enzyme with a peptide of the formula:

H-Asp-Phe-Val-Gln-Trp-Leu-Met-Asn-Thr-OH.

12. The peptide-enzyme conjugate as claimed in claim 11, wherein the conjugate is one obtained by coupling $\beta$-D-galactosidase with a peptide of the formula:

H-Asp-Phe-Val-Gln-Trp-Leu-Met-Asn-Thr-OH.

13. The peptide-enzyme conjugate as claimed in claim 11, wherein the conjugate is one obtained by coupling alkaline phosphatase with a peptide of the formula:

H-Asp-Phe-Val-Gln-Trp-Leu-Met-Asn-Thr-OH.

14. The peptide-enzyme conjugate as claimed in claim 9, wherein the conjugate is one obtained by coupling a labeling enzyme with a peptide of the formula
H-Asp-Ser-Arg-Arg-Ala-Gln-Phe-Val-Gln-Trp-Leu-Met-Asn-Thr-OH.

15. The peptide-enzyme conjugate as claimed in claim 14, wherein the conjugate is one obtained by coupling β-D-galactosidase with a peptide of the formula:
H-Asp-Ser-Arg-Arg-Ala-Gln-Asp-Phe-Val-Gln-Trp-Leu-Met-Asn-Thr-OH.

16. The peptide-enzyme conjugate as claimed in claim 14, wherein the conjugate is one obtained by coupling alkaline phosphatase with a peptide of the formula:
H-Asp-Ser-Arg-Arg-Ala-Gln-Asp-Phe-Val-Gln-Trp-Leu-Met-Asn-Thr-OH.

17. A method of enzyme immunoassay of pancreatic glucagon which comprises reacting a peptide-enzyme conjugate obtained by coupling a reactive substituent group of a labeling enzyme and of a peptide of the formula:

H-R$_3$-Phe-Val-Gln-Trp-Leu-Met-Asn-Thr-OH wherein R$_3$ is a peptide fragment selected from the group consisting of Asp, Gln-Asp, Ala-Gln-Asp, Arg-Ala-Gln-Asp, Arg-Arg-Ala-Gln-Asp, Ser-Arg-Arg-Ala-Gln-Asp, and Asp-Ser-Arg-Arg-Ala-Gln-Asp, a test fluid, a plasma and an anti-glucagon antibody competitively and measuring the amount of pancreatic glucagon in the test fluid by detecting the enzyme activity in the liquid or solid phase.

18. The method as claimed in claim 17, wherein the labeling enzyme is β-D-galactosidase or alkaline phosphatase.

19. The method as claimed in claim 17, wherein the peptide-enzyme conjugate is one obtained by coupling a labeling enzyme with a peptide of the formula:
H-Asp-Phe-Val-Gln-Trp-Leu-Met-Asn-Thr-OH.

20. The method as claimed in claim 17, wherein the peptide-enzyme conjugate is one obtained by coupling a labeling enzyme with a peptide of the formula:
H-Asp-Ser-Arg-Arg-Ala-Gln-Asp-Phe-Val-Gln-Trp-Leu-Met-Asn-Thr-OH.

* * * * *